United States Patent
Ueda

Patent Number: 5,183,718
Date of Patent: Feb. 2, 1993

[54] PHOTOSENSITIVE MEMBER COMPRISING SPECIFIC DISTYRYL COMPOUND

[75] Inventor: Hideaki Ueda, Kawanishi, Japan

[73] Assignee: Minolta Camera Kabushiki Kaisha, Osaka, Japan

[21] Appl. No.: 899,596

[22] Filed: Jun. 18, 1992

Related U.S. Application Data

[63] Continuation of Ser. No. 600,720, Oct. 22, 1990, abandoned.

[30] Foreign Application Priority Data

Oct. 23, 1989 [JP] Japan .................. 1-275443
Jun. 27, 1990 [JP] Japan .................. 2-170781

[51] Int. Cl.$^5$ .................. G03G 5/047; G03G 5/09
[52] U.S. Cl. .................. 430/59; 430/83
[58] Field of Search .................. 430/59, 83

[56] References Cited

U.S. PATENT DOCUMENTS

| | | |
|---|---|---|
| 3,820,989 | 6/1974 | Rule et al. |
| 4,465,857 | 8/1984 | Neumann et al. ............ 430/59 X |
| 4,477,550 | 10/1984 | Horie et al. ............ 430/59 |
| 4,606,988 | 8/1986 | Sasaki ............ 430/59 |
| 4,724,192 | 2/1988 | Makino et al. ............ 430/59 X |
| 4,988,596 | 1/1991 | Ueda ............ 430/59 |
| 5,013,623 | 5/1991 | Itoh et al. ............ 430/59 |

FOREIGN PATENT DOCUMENTS

| | | |
|---|---|---|
| 3814105 | 11/1988 | Fed. Rep. of Germany ........ 430/59 |
| 62-120346 | 6/1987 | Japan . |

*Primary Examiner*—Roland Martin
*Attorney, Agent, or Firm*—Burns, Doane, Swecker & Mathis

[57] ABSTRACT

The present invention relates to a photosensitive member comprising a specified distyryl compound represented by the general formula [I]:

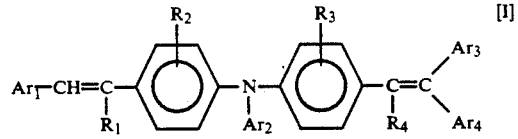

in which
Ar$_1$ is a hydrogen atom, an alkyl group, an aralkyl group, an alkenyl group, an alkynyl group, an aryl group, or a heterocyclic group, wherein the aryl group and the heterocyclic group may have a substituent;

Ar$_2$ is an alkyl group, an aralkyl group or an aryl group, each of which may have a substituent;

Ar$_3$ and Ar$_4$ are independently an alkyl group, an aryl group, an aralkyl group or a heterocyclic group, each of which may have a subsitutent;

R$_2$ is an alkyl group, an aralkyl group or an aryl group, each of which may have a substituent;

R$_1$ and R$_4$ are a hydrogen atom, an alkyl group, an aryl group, an aralkyl group;

R$_2$ $l$ and R$_3$ are a hydrogen atom, an alkyl group, an alkoxy group or a halogen atom.

18 Claims, 1 Drawing Sheet

PHOTOSENSITIVE MEMBER COMPRISING SPECIFIC DISTYRYL COMPOUND

This application is a continuation, of application Ser. No. 07/600,720, filed Oct. 22, 1990, now abandoned.

BACKGROUND OF THE INVENTION

This invention relates to a photosensitive member with a photosensitive layer comprising a new distyryl compound.

In general electrophotography, many methods for forming copied images are known. For example, the surface of a photosensitive member is charged and irradiated to form electrostatic latent images thereon, the electrostatic latent images are developed to visible images by a developer, and then the developed images are fixed directly onto the photosensitive member (this method is referred to as a direct method). Alternatively, developed electrostatic latent images on a photosensitive member which are made visible by a developer are transferred to a copying paper and then, the transferred images are fixed on the copying paper (this method is referred to as a powder transferring method). In another method, electrostatic latent images on a photosensitive member are transferred onto a copying paper, the transferred electrostatic latent images are developed by a developer and then fixed on the copying paper (referred to as an electrostatic latent image transferring method).

With respect to photosensitive materials conventionally used for forming a photosensitive layer, inorganic photoconductive materials such as selenium, cadmium sulfide, zinc oxide and the like are known.

These photoconductive materials have many advantages, such as ability to be charged to an adequate potential, low loss of electrical charges in the dark, a rapid dissipation of electrical charges with irradiation of light and the like. However, they have disadvantages. For example, a photosensitive member based on selenium is difficult to produce, has high production costs and difficult to handle due to inadequate resistivity to heat or mechanical impact. A photosensitive member based on cadmium sulfide or zinc oxide has defects such as its unstable sensitivity in a highly humid environmental and loss of stability with time because of the deterioration of dyestuffs, added as a sensitizer, by corona charge and fading with exposure.

Many kinds of organic photoconductive materials such as polyvinylcarbazole and so on have been proposed. These organic photoconductive materials have superior film forming properties, are light in weight, etc., but inferior in sensitivity, durability and environmental stability compared to the aforementioned inorganic photoconductive materials.

A photoconductive organic compound of low molecular weight is preferable in that electrophotographic properties or physical properties of a layer can be controlled by selecting the kind of binder resin, composition ratio or the like, but the high compatibility of the photoconductive organic compound with the binder resin is required because the photoconductive organic compound is used in combination with the binder resin.

A photosensitive member with an photoconductive organic compound of high molecular weight or low molecular weight dispersed in a binder resin has defects, such as high residual potential caused by many traps of carriers, low sensitivity or the like. In order to overcome those defects, it has been proposed that the photoconductive compound is used together with a charge transporting material.

Further, a function-divided photosensitive member has been proposed, in which charge generating function and charge transporting function are showed by separate materials. In such a function-divided photosensitive member, many kinds of organic compounds are proposed as a charge transporting material incorporated in a charge transporting layer. But, they have various problems in actual act. For example, U.S. Pat. No. 3,189,447 proposes use of 2,5-bis(p-diethylaminophenyl)-1,3,4-oxadiazole, but this compound has only a poor compatibility with binders and is liable to separate out as crystals. Further U.S. Pat. No. 3,820,989 discloses use of diarylalkane derivatives having a high compatibility with binders. However, the photosensitive member containing the derivatives undergoes variations in sensitivity when repeatedly used. Japanese Patent Laid-Open No. 54-59143 discloses a hydrazone compound, which show relatively good residual potential properties. However, the hydrazone compound is inferior in chargeability, repetition properties or the like.

As above mentioned, the fact is that there are almost no preferable organic compound of low molecular weight suitable for practical use.

Japanese Patent Laid-Open Nos. 60-175052 and 62-120346 disclose a distyryl compound excellent in chargetransportability, but the distyryl compound is completely different from the compound of the present invention disclosed below.

SUMMARY OF THE INVENTION

The object of the invention is to provide a photosensitive member excellent in sensitivity, chargeability, fatigue properties when used repeatedly, stability in electrophotographic properties by incorporating a specified distyryl compound with excellent mutual solubility with a binder resin and excellent charge transportability.

This invention relates to a photosensitive member comprising an electrically conductive substrate; and a photosensitive layer formed on or over the substrate and including a distyryl compound represented by the general formula [I]

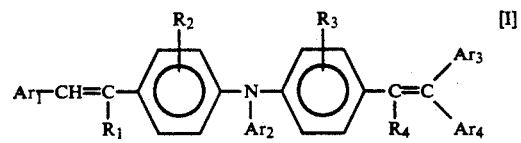

in which $Ar_1$ is a hydrogen atom, an alkyl group, an aralkyl group, an alkenyl group, an alkynyl group, an aryl group, or a heterocyclic group, wherein the aryl group and the heterocyclic group may have a substituent;

$Ar_2$ is an alkyl group, an aralkyl group or an aryl group, each of which may have a substituent;

$Ar_3$ and $Ar_4$ are independently an alkyl group, an aryl group, an aralkyl group or a heterocyclic group, each of which may have a substituent;

$R_2$ is an alkyl group, an aralkyl group or an aryl group, each of which may have a substituent;

$R_1$ and $R_4$ are a hydrogen atom, an alkyl group, an aryl group, an aralkyl group;

$R_2$ and $R_3$ are a hydrogen atom, an alkyl group, an alkoxy group or a halogen atom.

DETAILED DESCRIPTION OF THE INVENTION

Figure 1:
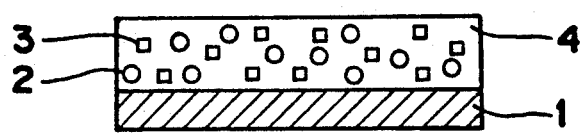
FIG. 1 is a diagram showing the structure of dispersion-type photosensitive member embodying the invention comprising a photosensitive layer formed on an electrically conductive substrate.

The present invention provides a photosensitive member excellent in sensitivity, charge transportability, initial surface potential, potential reducing ratio in the dark, light-fatigue properties when used repeatedly.

The present invention has accomplished the above object by the introduction of a specific distyryl compound excellent in mutual solubility with a binder resin and charge transportability into a photosensitive member as a charge transporting material.

A photosensitive member provided according to the present invention contains a specific distyryl compound represented by the following formula [I]

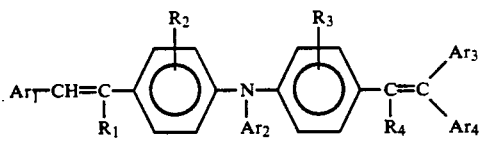

In the general formula [I], $Ar_1$ is a hydrogen atom, an alkyl group, such a methyl, ethyl or the like, an aryl group, such as phenyl, naphthyl or the like, an aralkyl group, such as benzyl or the like, a heterocyclic ring group, such as a residual group of thiophene, furan or the like, an alkenyl group, such as ethenyl or the like, or an alkynyl group, such as ethynyl or the like. The aryl group and the heterocyclic group may have a substituent, such as an alkyl group, an alkoxy group, a hydroxy group, disubstituted amino group or the like. Preferable $Ar_1$ is a hydrogen atom, a $C_1$–$C_4$ lower alkyl group, a benzyl group, an ethenyl group, an ethynyl group, a phenyl group which may have a substituent, a thienyl group, a furyl group, a pyrrolyl group, a pyridyl group or the like.

$Ar_2$ is a lower alkyl group, such as methyl or the like, an aralkyl group, such as benzyl or the like, an aryl group, such as phenyl or the like. These groups may have a substituent, such as an alkyl group, an alkoxy group, a halogen atom or the like.

$Ar_3$ and $Ar_4$ are independently a lower alkyl group, such as methyl, ethyl or the like, an aralkyl group, such as benzyl or the like, an aryl group, such as phenyl, tolyl, naphthyl or the like, a heterocyclic group, such as a residual group of thiophene, dioxaindane, benzothiazole or the like. These groups may have a substituent, such as an alkyl group, an alkoxy group, a hydroxy group, a disubstituted amino group, a halogen atom or the like.

$R_1$ and $R_4$ are independently a hydrogen atom, an alkyl group, such as methyl, ethyl or the like, an aryl group, such as phenyl or the like, an aralkyl group, such as benzyl or the like.

$R_2$ and $R_3$ are independently a hydrogen atom, an alkyl group, such as methyl or the like, an alkoxy group, such as methoxy, ethoxy or the like, an aralkyl group, such as benzyl or the like, a halogen atom, such as chlorine or the like.

A distyryl compound represented by the general formula [I] is asymmetric at the center of the nitrogen atom. The distyryl compound effects the improvement of solubility in resin, electrophotographic properties, such as sensitivity, repetition properties and the like. $Ar_3$ and $Ar_4$ as above mentioned effect the improvement of compatibility with resin and coating properties. Further, sensitivity becomes good because π-electron system expands. When $Ar_1$ is selected from the ones as above mentioned, the molecular does not become so large in size. Therefore, the deterioration of compatibility or coating properties can be prevented.

Preferable distyryl compounds among the styryl compounds represented by the general formula [I] are the one represented by the general formula [II] or the general formula [III] below

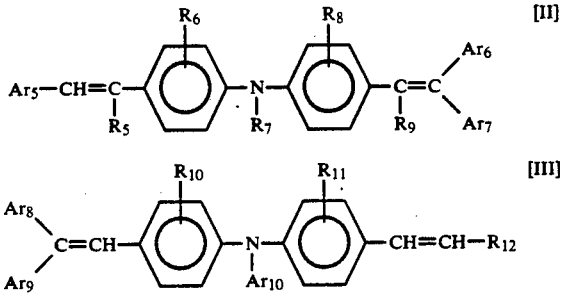

In the general formula [II], $Ar_5$ and $Ar_6$ are independently an aryl group, such as phenyl, tolyl, naphthyl or the like, a heterocyclic group, such as a residual group of thiophene, dioxaindane, benzothiazole or the like. These groups may have a substituent, such as an alkyl group, an alkoxy group, a hydroxy group, disubstituted amino group or the like.

$R_7$ and $Ar_7$ are independently a lower alkyl group, such as methyl, ethyl or the like, an aryl group, such as phenyl or the like, an aralkyl group, such as benzyl or the like. These groups may have a substituent, such as an alkyl group, an alkoxy group or the like.

$R_6$ and $R_8$ are independently a hydrogen atom, an alkyl group, such as methyl or the like, an aralkyl group, such as benzyl or the like, a halogen atom, such as chlorine or the like.

$R_5$ and $R_9$ are independently a hydrogen atom, an alkyl group, such as methyl or the like, an aralkyl group, such as benzyl or the like, or an aryl group, such as phenyl or the like.
Examples of more preferable distyryl compounds represented by the general formula [II] are those having the following structural formulas. These examples are in no way limitative.
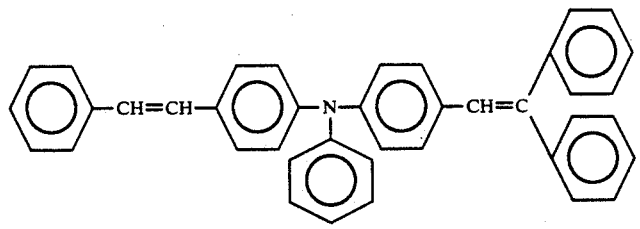
[II-1]
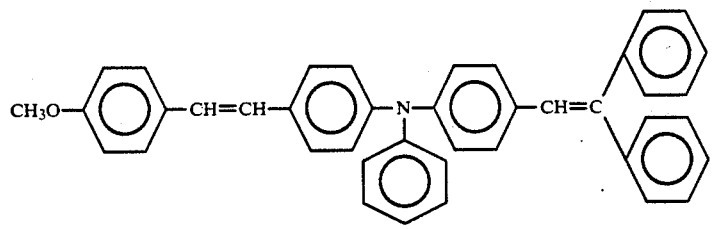
[II-2]
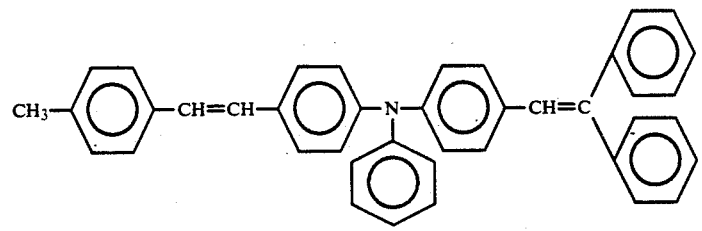
[II-3]
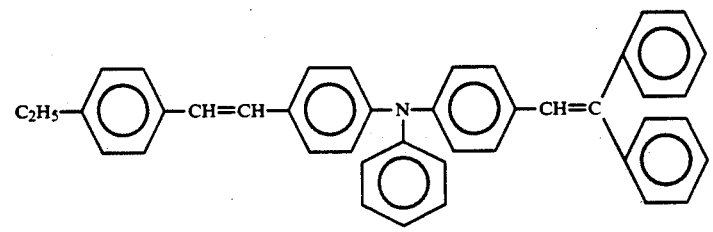
[II-4]
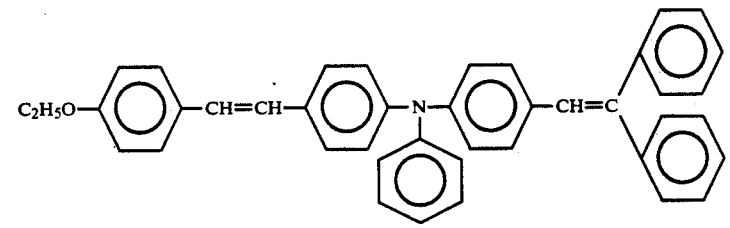
[II-5]
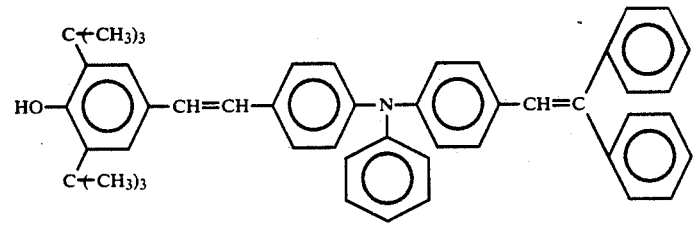
[II-6]

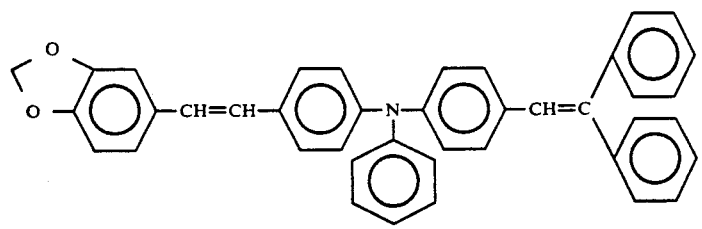
[II-7]
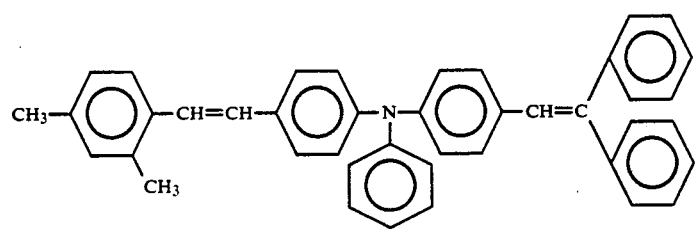
[II-8]
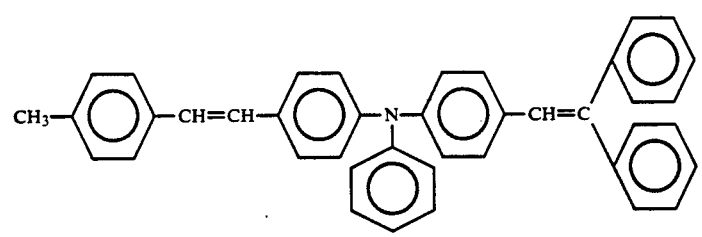
[II-9]
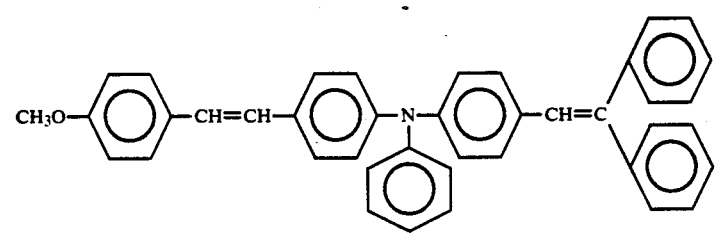
[II-10]
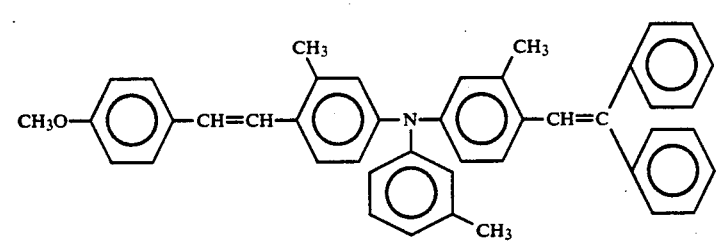
[II-11]
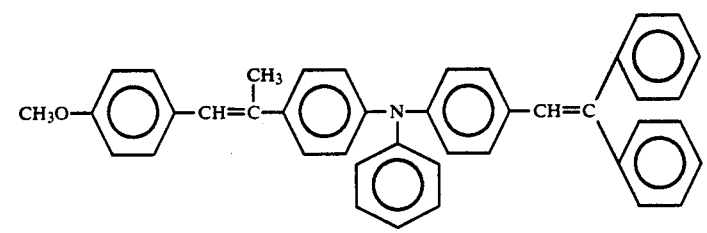
[II-12]

-continued
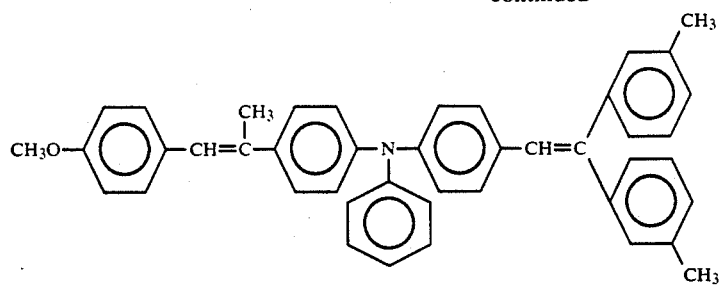
[II-13]
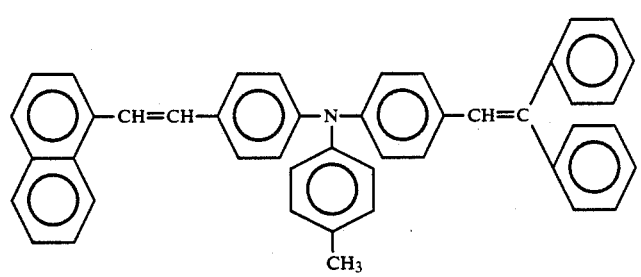
[II-14]
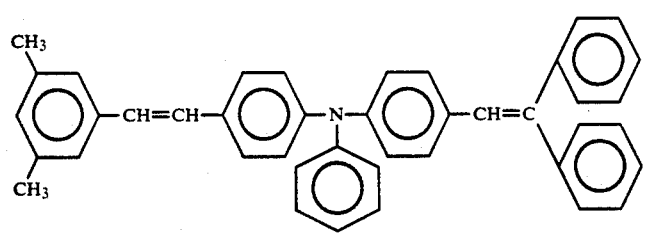
[II-15]
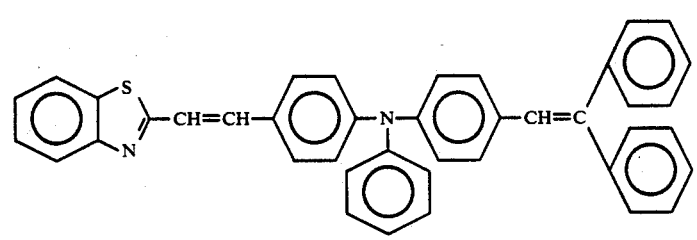
[II-16]
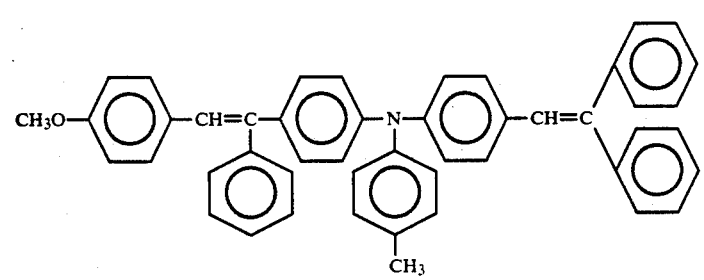
[II-17]
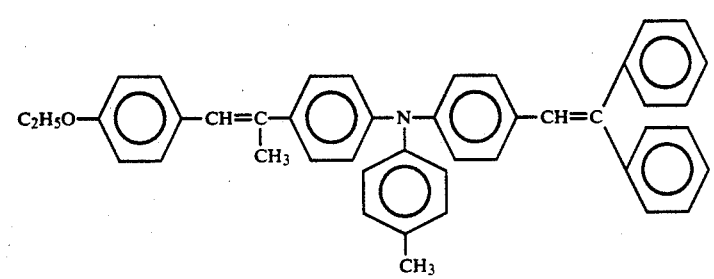
[II-18]

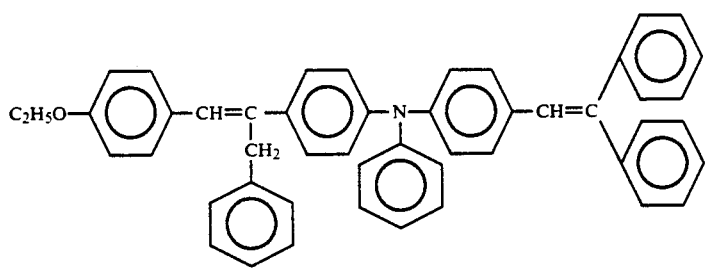
[II-19]
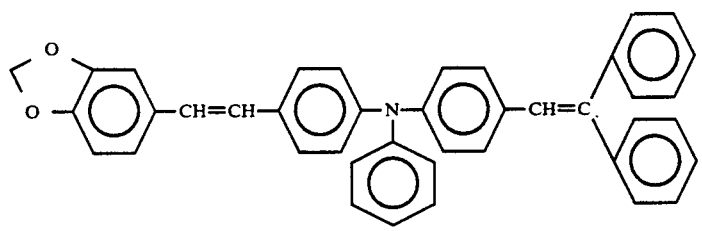
[II-20]
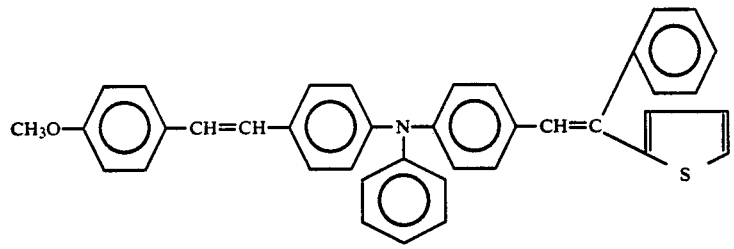
[II-21]
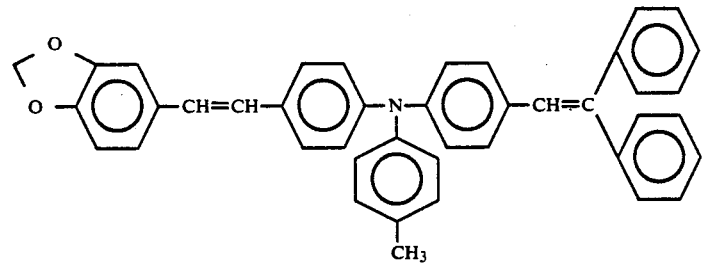
[II-22]
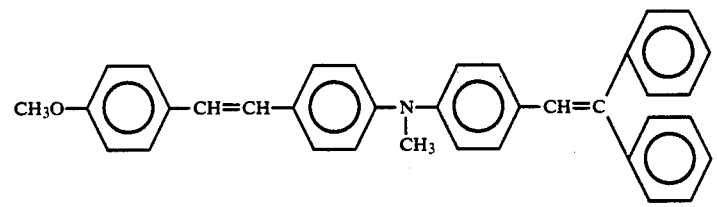
[II-23]
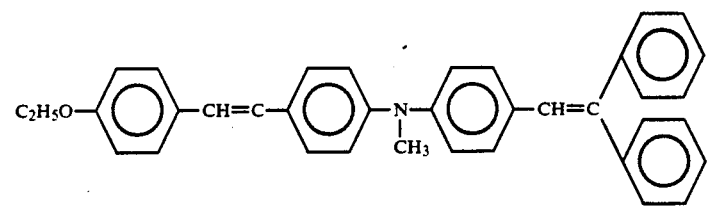
[II-24]

-continued
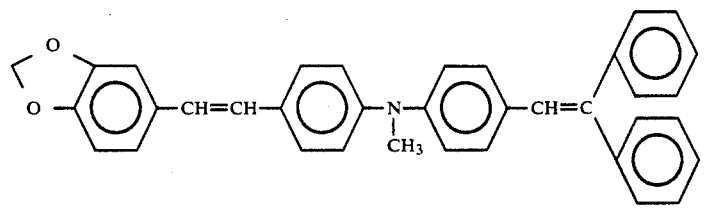
[II-25]
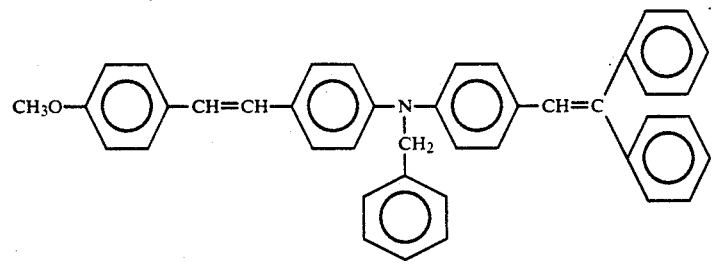
[II-26]
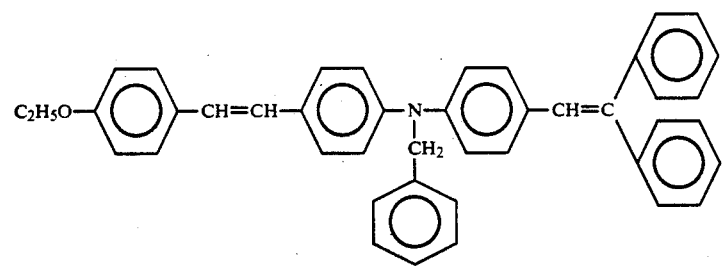
[II-27]
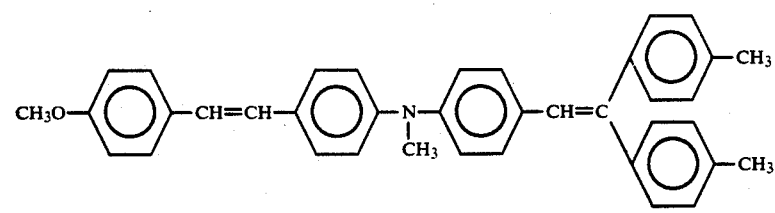
[II-28]
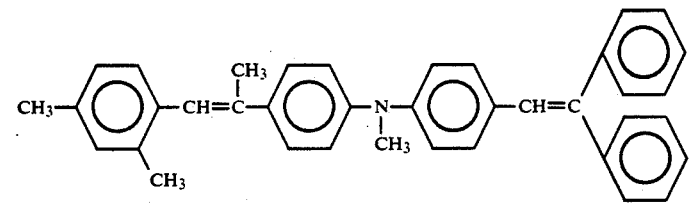
[II-29]
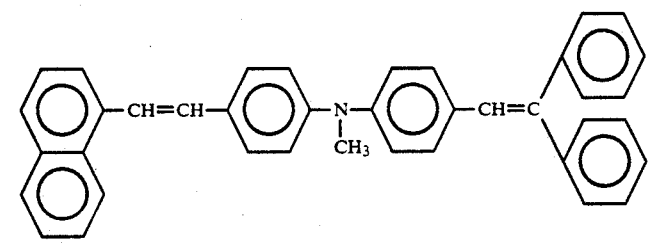
[II-30]
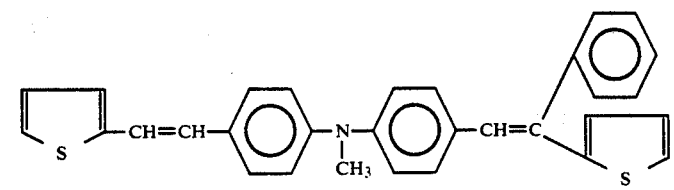
[II-31]

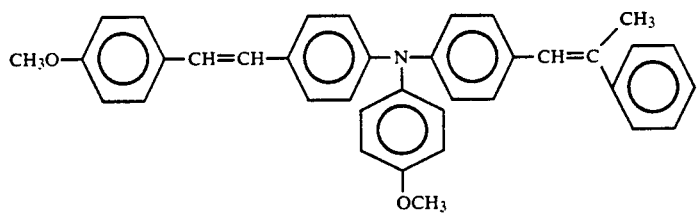
[II-32]
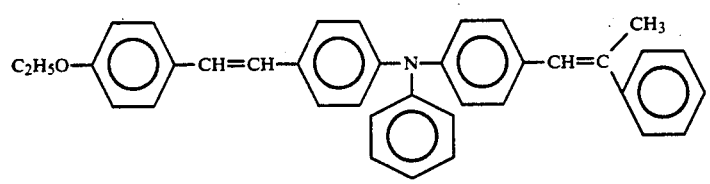
[II-33]
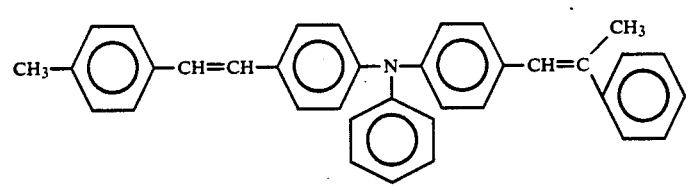
[II-34]
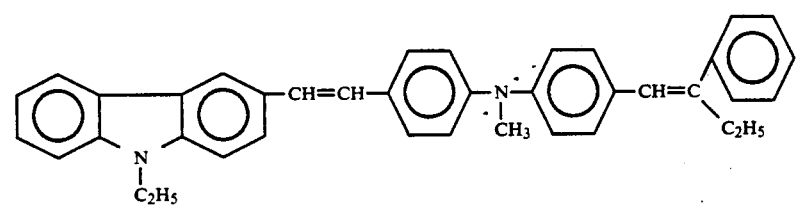
[II-35]
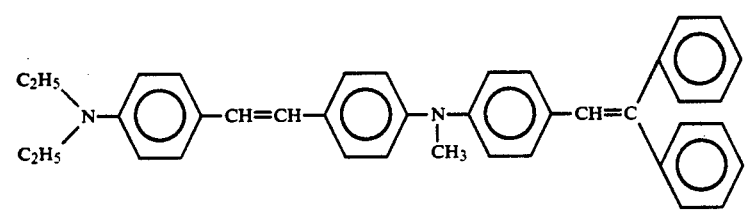
[II-36]
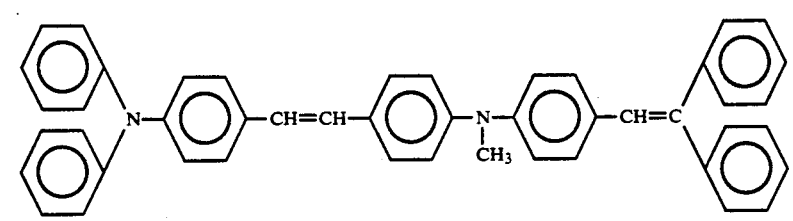
[II-37]
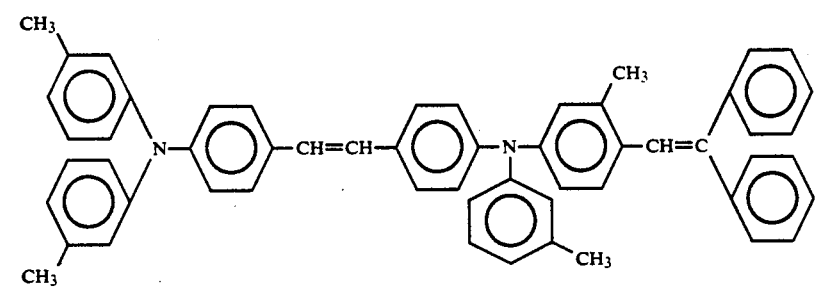
[II-38]

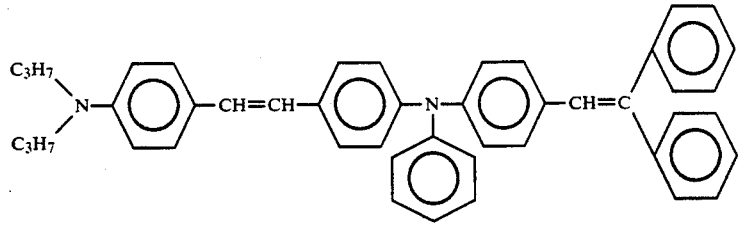

[II-39]

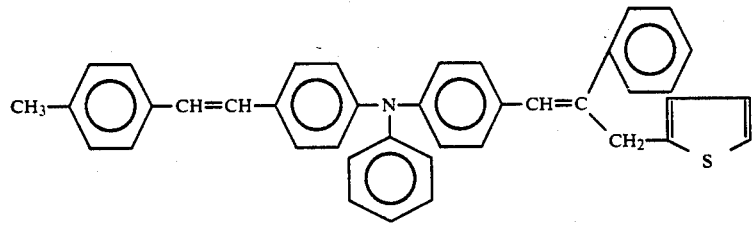

[II-40]

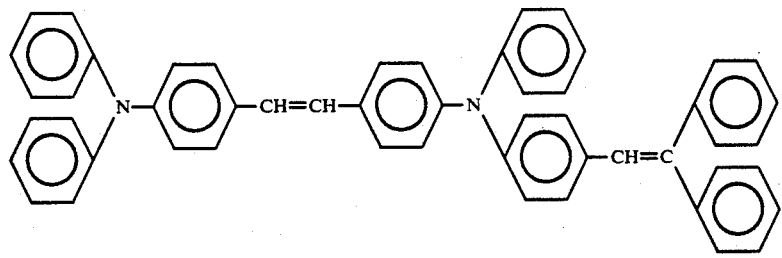

[II-41]

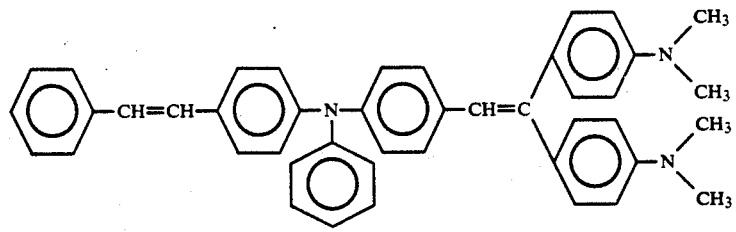

[II-42]

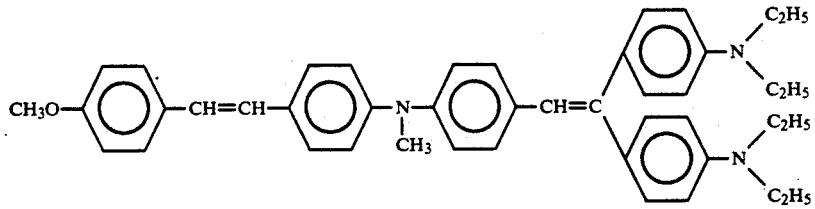

[II-43]

In the general formula [III], $Ar_8$ and $Ar_9$ are independently a lower alkyl group, such as methyl, ethyl or the like, or an aryl group, such as phenyl, tolyl, naphthyl or the like. These groups may have a substituent, such as an alkyl group, an alkoxy group, a hydroxy group, a disubstituted amino group, a halogen atom or the like.

$Ar_{10}$ is a lower alkyl group, such as methyl or the like, an aralkyl group, such as benzyl or the like, or an aryl group, such as phenyl or the like. These groups may have a substituent, such as an alkyl group, an alkoxy group, a halogen atom or the like.

$R_{10}$ and $R_{11}$ are independently a hydrogen atom, an alkyl group, such as methyl or the like, an alkoxy group, such as methoxy, ethoxy or the like, a halogen atom, such as chlorine or the like.

$R_{12}$ is a hydrogen atom, an alkyl group, such as methyl, ethyl or the like, an aralkyl group, such as benzyl or the like, a heterocyclic ring group, such as a residual group of thiophene, furan, pyrrole, pyridine or the like, an alkenyl group, such as ethenyl or the like, an alkynyl group, such as an ethynyl group or the like.

Examples of more preferred distyryl compounds represented by the general formula [III] are those having the following structural formulas. These examples are in no way limitative.

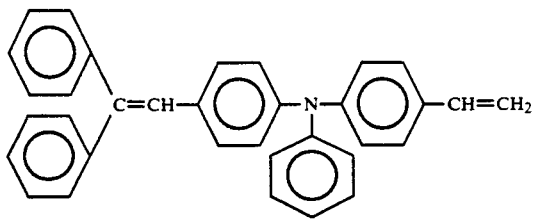
[III-1]
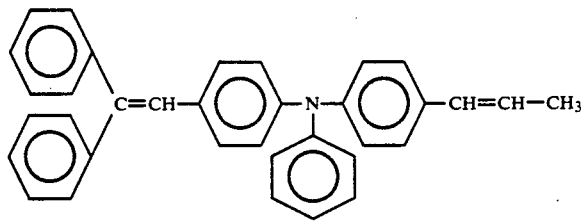
[III-2]
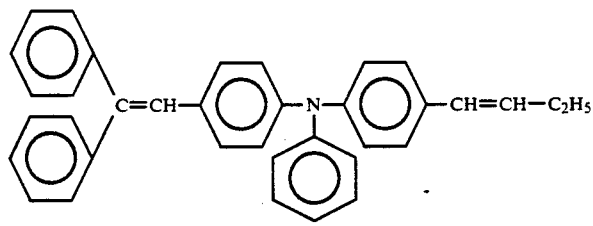
[III-3]
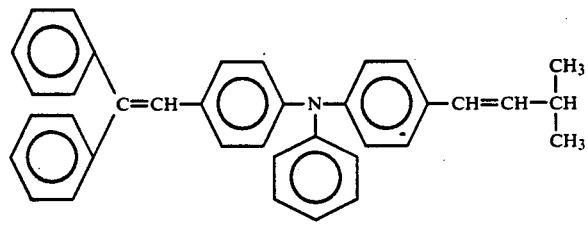
[III-4]
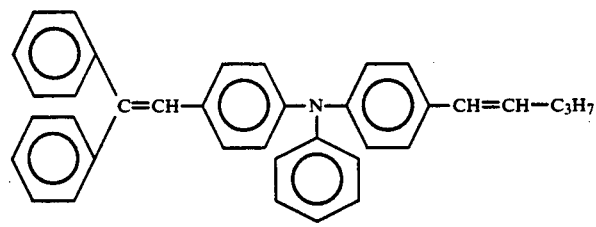
[III-5]
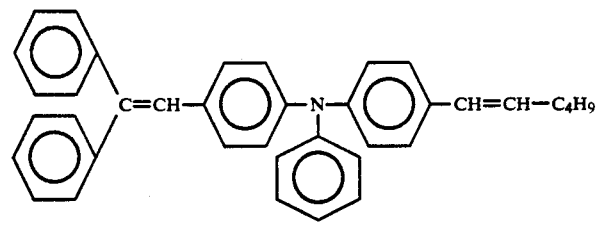
[III-6]
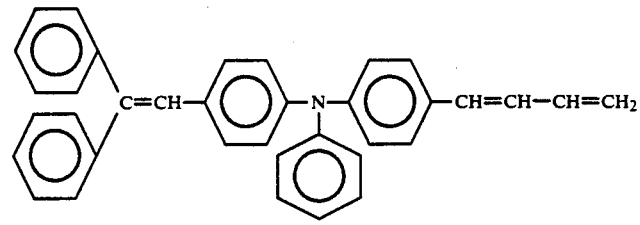
[III-7]

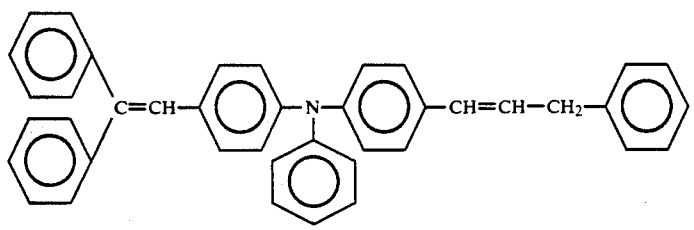
[III-8]
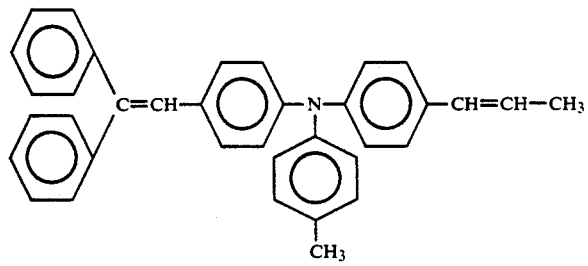
[III-9]
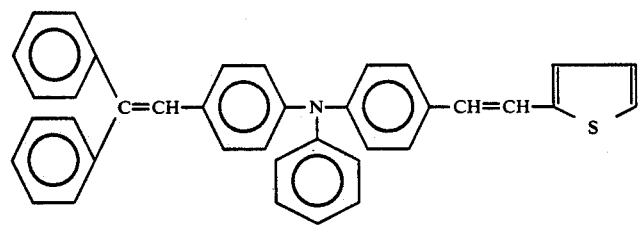
[III-10]
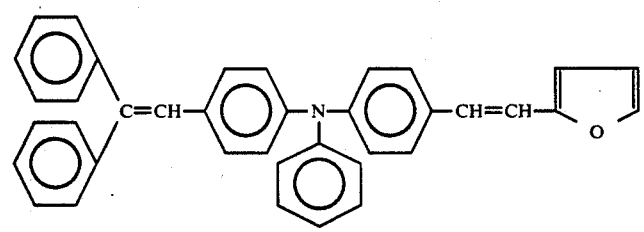
[III-11]
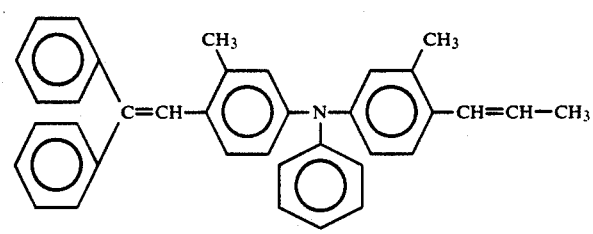
[III-12]
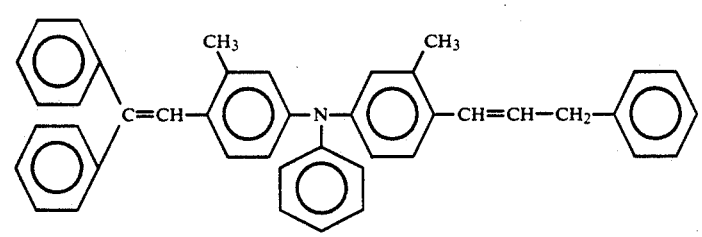
[III-13]

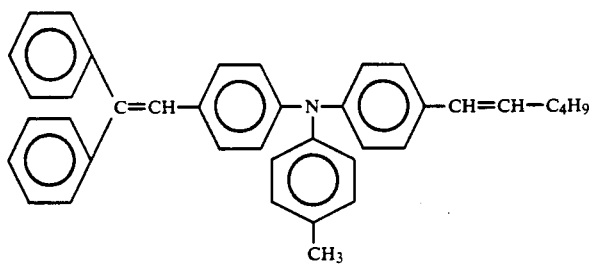
[III-14]
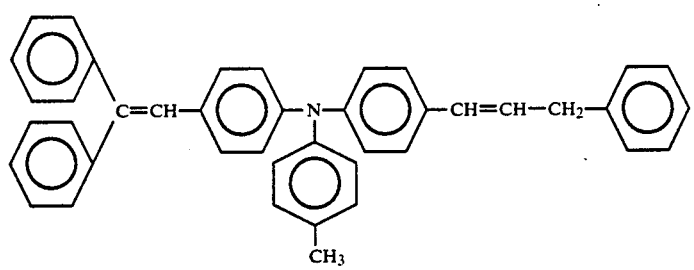
[III-15]
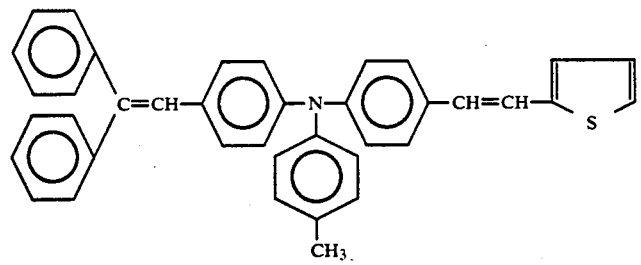
[III-16]
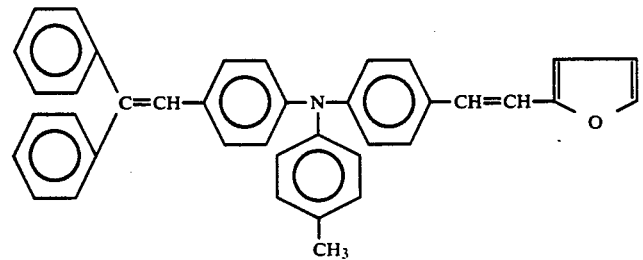
[III-17]
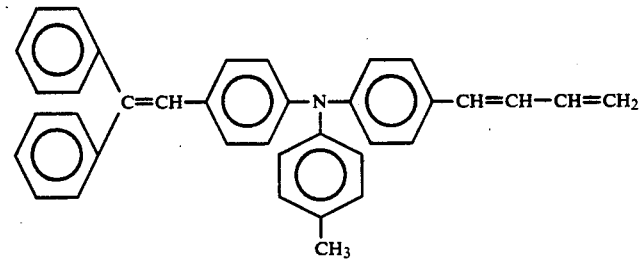
[III-18]
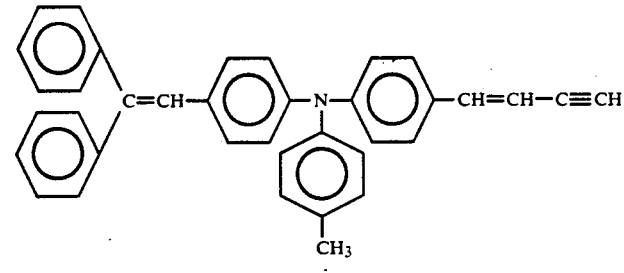
[III-19]

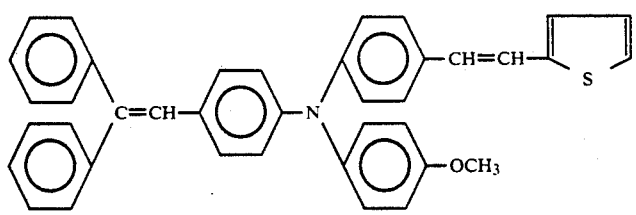
[III-20]
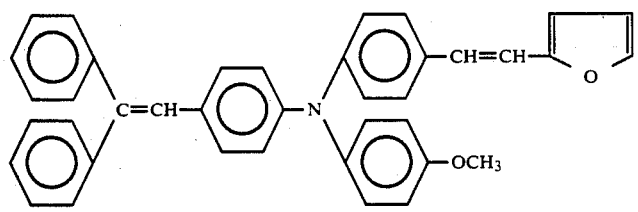
[III-21]
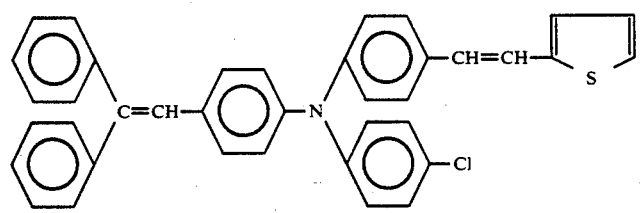
[III-22]
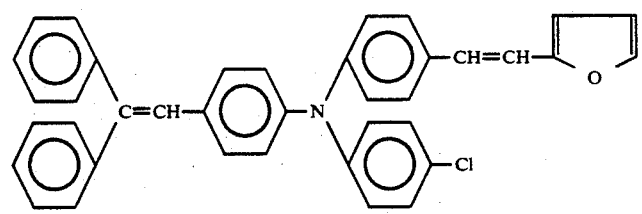
[III-23]
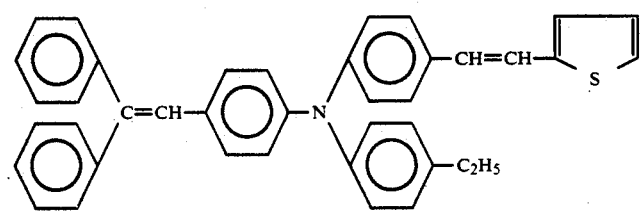
[III-24]
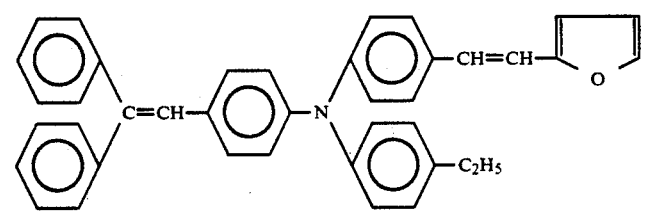
[III-25]
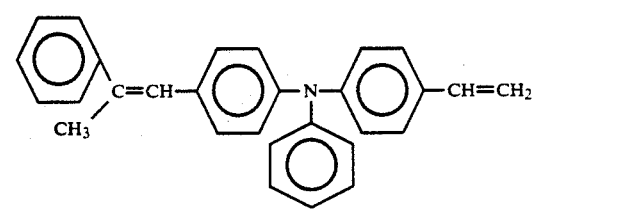
[III-26]

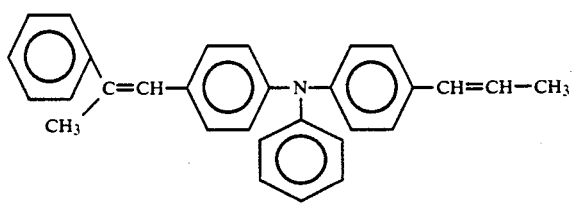
[III-27]
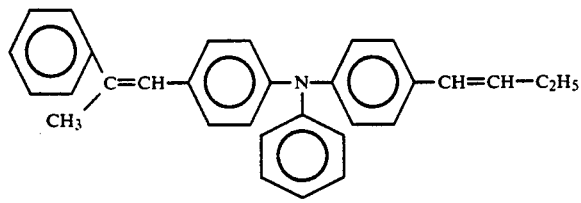
[III-28]
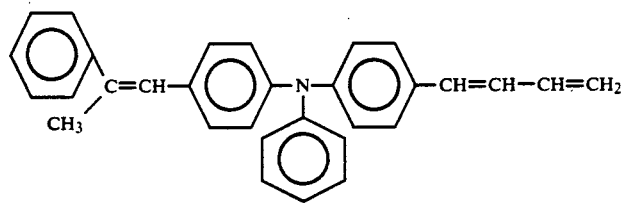
[III-29]
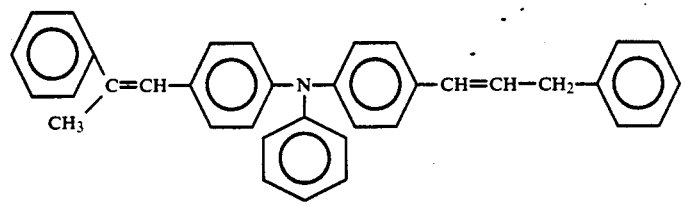
[III-30]
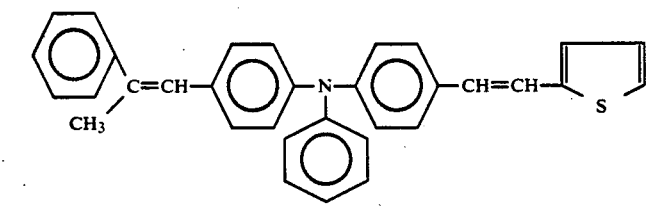
[III-31]
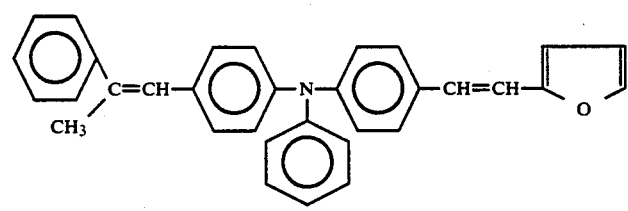
[III-32]
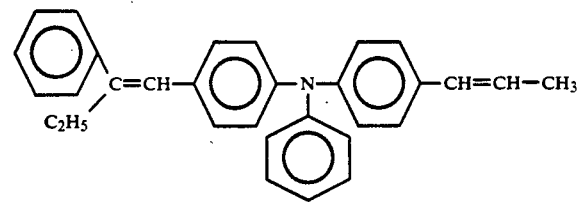
[III-33]

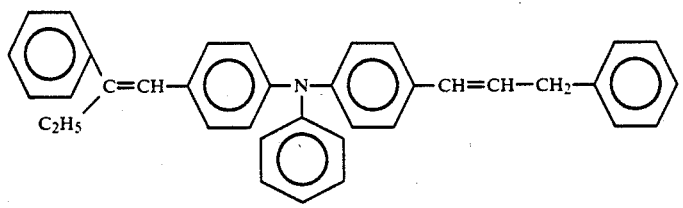
[III-34]
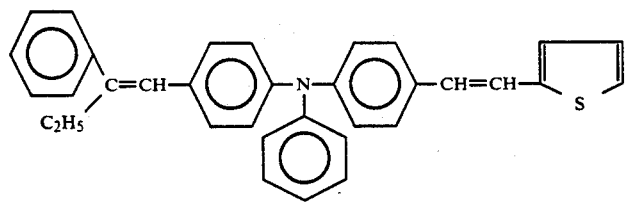
[III-35]
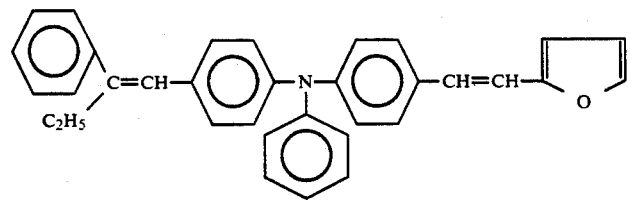
[III-36]
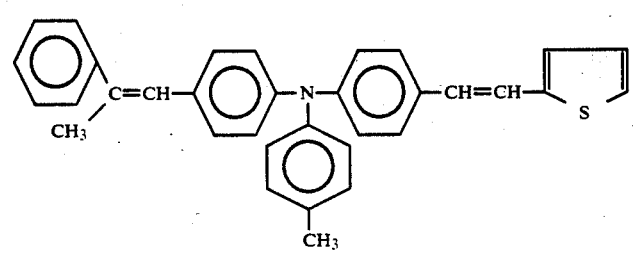
[III-37]
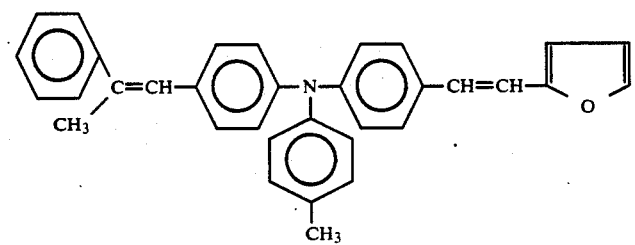
[III-38]
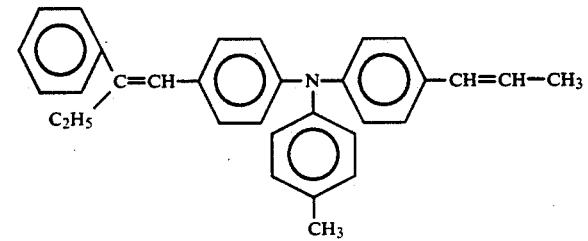
[III-39]

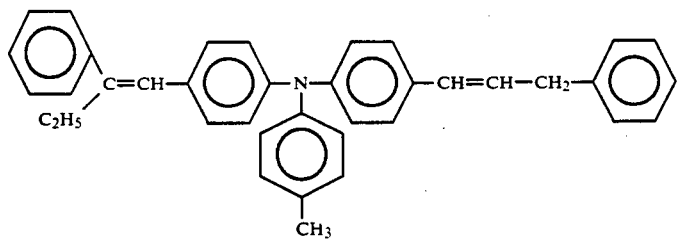
[III-40]
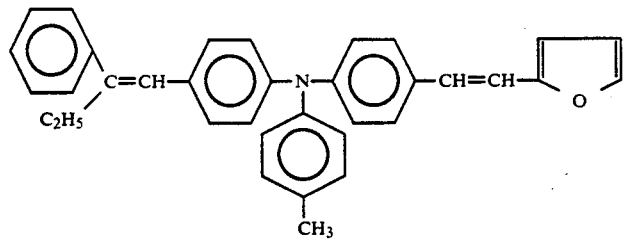
[III-41]
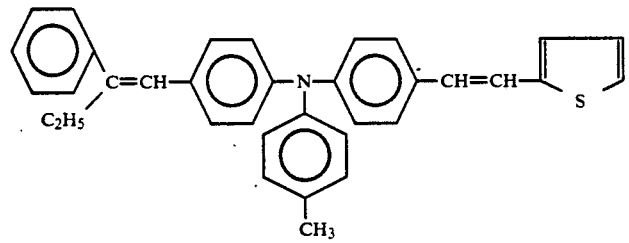
[III-42]
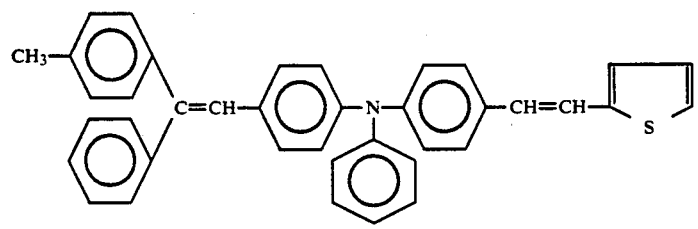
[III-43]
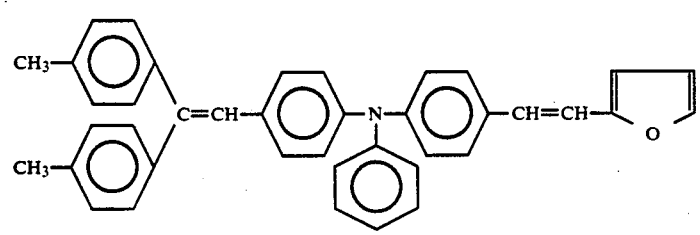
[III-44]
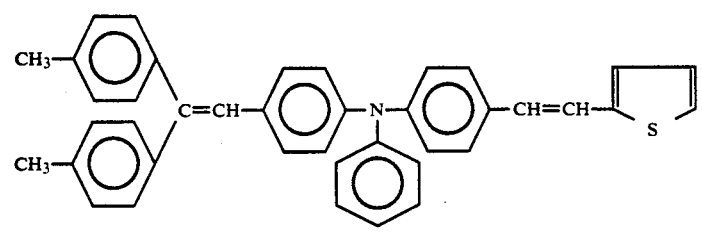
[III-45]

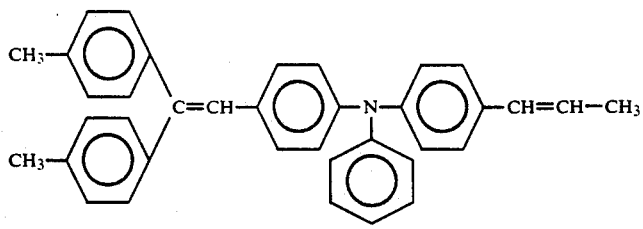
[III-46]
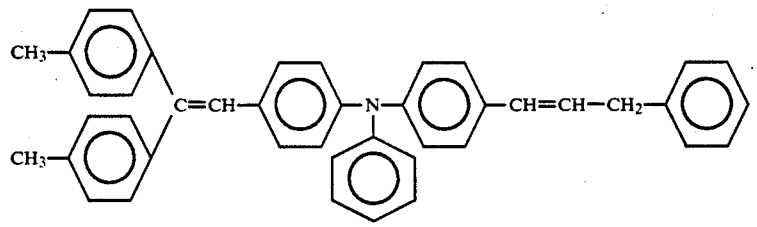
[III-47]
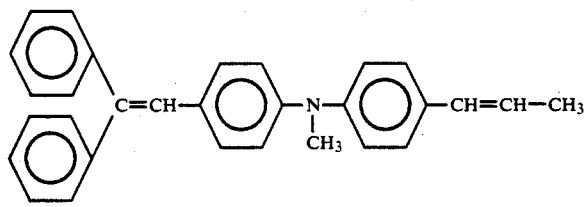
[III-48]
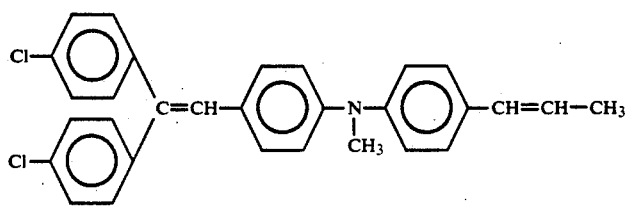
[III-49]
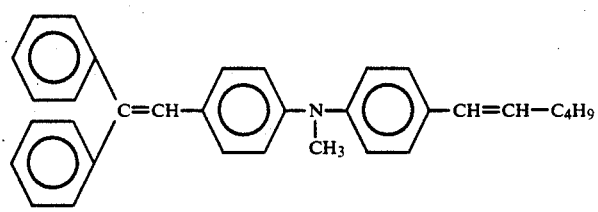
[III-50]
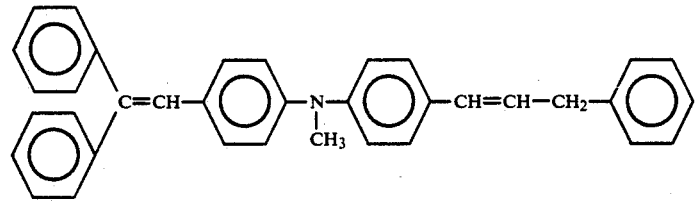
[III-51]
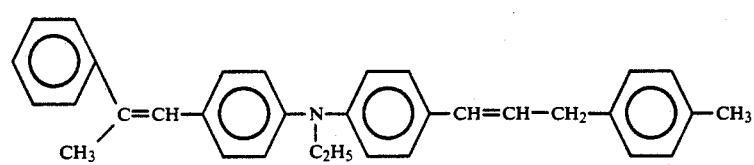
[III-52]

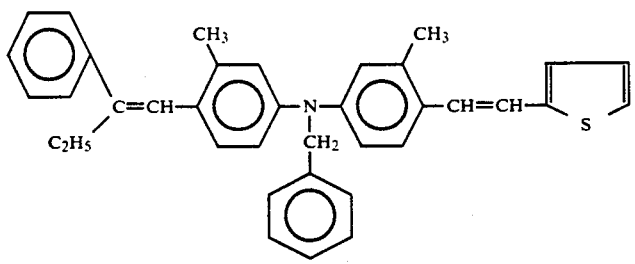
[III-53]
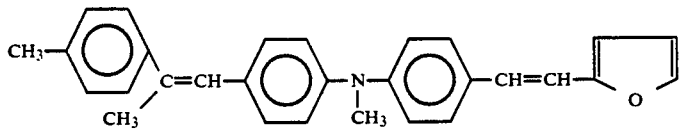
[III-54]
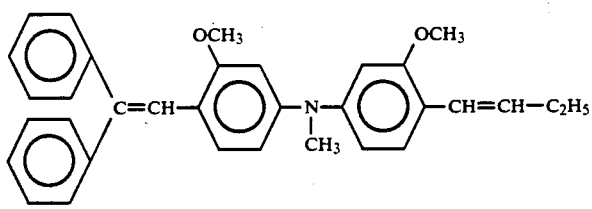
[III-55]
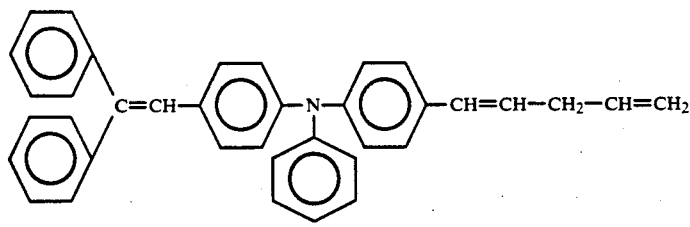
[III-56]
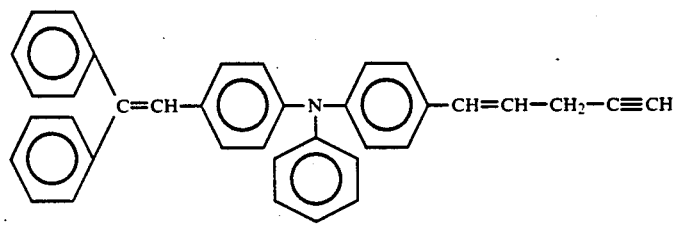
[III-57]
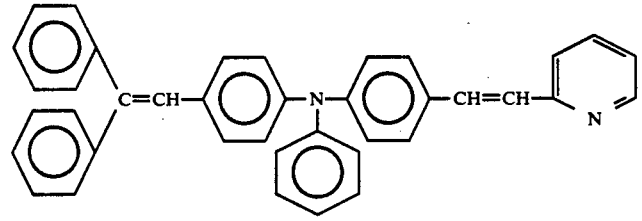
[III-58]
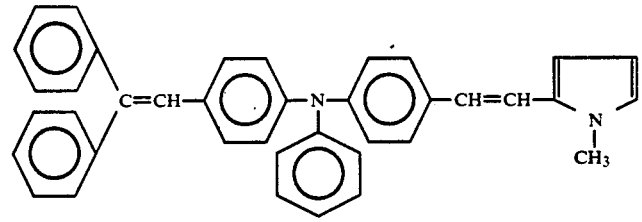
[III-59]

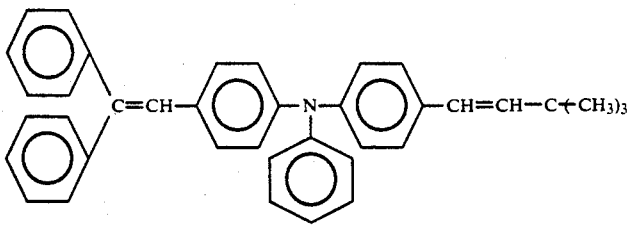

[III-60]

Distyryl compounds, particularly excellent in compatibility with resin among the distyryl compound [II-1]- [II-43] and [III-1]- [III-60] are the ones numbered by [II-1]- [II-10], [II-15], [II-20]- [II-22], [II-26], [II-27], [II-32]- [II-34], [II-40] and [III-1]- [III-47].

A distyryl compound represented by the general formula [I] may be synthesized by a known method.

For example, an aldehyde or a ketone compound represented by the general formula [IV]

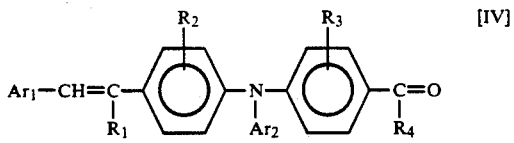

in which $Ar_1$, $Ar_2$, $R_1$-$R_4$ are the same as those in the formula [I] is condensed with a phosphorous compound represented by the general formula [V]

in which X is trialkyl phosphonium compound or triaryl phosphonium compound represented by the following formula below;

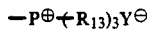

or dialkyl phosphite or diaryl phosphite represented by the following formula below;

$PO(OR_{14})_2$ in which Y is a halogen atom; $R_{13}$ and $R_{14}$ are respectively an alkyl or an aryl group.

An aldehyde or a ketone compound represented by the general formula [VI]

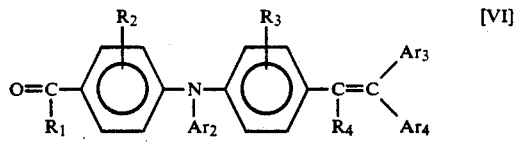

may be condensed with phosphorous compound represented by the general formula [VII]

$Ar_1$—$CH_2X$ [VIII]

in which $R_1$-$R_4$, $Ar_1$-$Ar_4$ are the same as those in the formula [I], and X is the same as that in the formula [V].

Examples of reaction solvents useful for the foregoing process are hydrocarbons, alcohols and ethers, such as methanol, ethanol, isopropanol, butanol, 2-methoxyethanol, 1,2-dimethoxyethane, bis(2-methoxyethyl) ether, dioxane, tetrahydrofuran, toluene, xylene, dimethyl sulfoxide, N,N-dimethylformamide, N-methylpyrrolidone, 1,3-dimethyl-2-imidazolizinone, etc.. Among these solvents, polar solvents, such as N,N-dimethylformamide and dimethyl sulfoxide are especially preferable.

Examples of useful condensing agents are sodium hydroxide, potassium hydroxide, sodium amide, sodium hydride, and alcoholates, such as sodium methoxide, potassium-t-butoxide, etc..

The reaction temperature can be selected from a wide range of from about 0° C. to about 100° C. and is preferably 10° C. to 80° C.

A photosensitive member of the present invention has a photosensitive layer comprising one or more distyryl compounds represented by the general formula [I].

The present invention may be applied to any type of photosensitive members per se known. For example, there is known a photosensitive member of a monolayer type with a charge generating material and distyryl compound dispersed in a binder resin on a substrate, or a so-called laminated type with a charge generating layer containing a charge generating material as a main component on a substrate and a charge transporting layer on the charge generating layer. A distyryl compound of the present invention is a photoconductive material and functions as a charge transporting material, which transports effectively charge carriers generated by absorbing light.

In order to form a photosensitive member of a monolayer type, fine particles of a charge generating material are dispersed in a solution of resin or a solution containing a distyryl compound as a charge transporting compound and resin. The dispersion solution is coated on the electrically conductive substrate and dried. The thickness of a photosensitive layer is 3–30 μm, preferably 5–20 μm. The sensitivity is poor if the distyryl compound as a charge transporting material and a charge generating material are used in an insufficient quantity. The chargeability becomes poor and the mechanical strength of photosensitive layer is inadequate if used to excess. The amount of the charge generating compound is contained at the content of 0.01-2 parts by weight, preferably 0.2-1.2 parts by weight on the basis of one part by weight of the resin.

In order to form a photosensitive member of a laminated type, a charge generating material is deposited in a vacuum on an electrically conductive substrate, a charge generating material is dissolved in a solvent such as amine to apply onto an electrically conductive substrate or an coating solution containing a charge generating material and, if necessary, binder resin dissolved in an appropriate solvent is applied onto an electrically conductive substrate to be dried, for the formation of a charge generating layer on the electrically conductive substrate. Then, a solution containing a charge transporting material and a binder resin is applied onto the charge generating layer followed by drying for the formation of a charge transporting layer. The charge generating materials suitable for the deposition in a vacuum include, for example, phthalocyanines, such as metal-free phthalocyanines, titanyl phthalocyanines, alumichlorophthalocyanines and the like, while the charge generating materials suitable for dispersion include, for example, bisazo pigments and the like. The thickness of a charge generating layer is 4 μm or less, preferably, 2 μm or less. It is suitable that the charge-transporting layer has a thickness in the range 3-30 μm, preferably 5-20 μm.

The content of charge transporting materials in the charge transporting layer is 0.2-2 parts by weight, preferably 0.3-1.3 parts by weight on the basis of one part by weight of the binder resin.

A photosensitive member of the present invention permits, in combination with a binder resin, the use of a plasticizer, such as halogenated paraffin, polybiphenyl chloride, dimethyl naphthalene, dibutyl phthalate o-terphenyl or the like, the use of an electron-attractive sensitizer, such as chloranil, tetracyanoethylene, 2,4,7-trinitro-fluorenone, 5,6-dicyanobenzoquinone, tetracyanoquinodimethane, tetrachlorophthalic anhydride, 3,5-dinitrobenzoic acid or the like, and the use of a sensitizer, such as methyl violet, rhodamine B, cyanine dye, pyrylium salt, thiapyrylium salt or the like.

An anti-oxidizing agent, an ultraviolet light absorber, a dispersing agent, an anti settling agent, a levelling agent and the like may be contained in a photosensitive member. A general transporting material, such as hydrazone compounds, or the like, may be used in combination a distyryl compound of the present invention.

Some examples of suitable binders for the production of a photosensitive member are thermoplastic resins, such as saturated polyesters, polyamides, acrylic resins, ethylene-vinyl acetate copolymers, ion cross-linked olefin copolymers (ionomer), styrene-butadiene block copolymers, polycarbonates, vinyl chloride-vinyl acetate copolymers, cellulose esters, polyimides, styrols, etc., and thermosetting resins, such as epoxy resins, urethane resins, silicone resins, phenolic resins, melamine resins, xylene resins, alkyd resins, thermosetting acrylic resins, etc., and photocuring resins, and photoconductive resins, such as poly-N-vinyl carbazoles, polyvinyl pyrenes, polyvinyl anthracenes, polyvinyl pyrroles, etc., all named without any significance of restricting the use to them. Any of these resins can be used singly or in combination with other resins. It is desirable for any of these electrically insulating resins to have a volume resistance of $1 \times 10^{12}$ Ω·cm or more when measured singly.

Examples of charge generating materials are organic substances, such as bisazo pigments, triarylmethane dyes, thiazine dyes, oxazine dyes, xanthene dyes, cyanine coloring agents, styryl coloring agents, pyrylium dyes, azo pigments, quinacridone pigments, indigo pigments, perylene pigments, polycyclic quinone pigments, bisbenzimidazole pigments, indanthrone pigments, squalylium pigments, azulene dye stuff, phthalocyanine pigments and the like, and inorganic substances, such as selenium, selenium-tellurium, selenium.arsenic, cadmium sulfide, cadmium selenide, amorphous silicon and the like. Any other material is also usable insofar as it generates charge carriers very efficiently upon absorption of light.

An electrically conductive substrate is exemplified by a sheet or a drum made of metal or alloy, such as copper, aluminum, silver, iron, nickel or the like; a substrate such as a plastic film on which the foregoing metal or alloy is adhered by a vacuum-deposition method or an electroless plating method and the like; a substrate such as a plastic film and paper on which an electro-conductive layer is formed by applying or deposition electroconductive polymer, indium oxide, tin oxide etc..

FIG. 1 to FIG. 5 schematically show examples of electrophotographic photosensitive members prepared with use of distyryl compound of the invention.

FIG. 1 shows a photosensitive member comprising a photosensitive layer 4 formed on a substrate 1 and prepared from a charge generating material 3 and a charge transporting material 2 as admixed with a binder. A distyryl compound of the invention is used as the charge transporting material.

Figure 2:
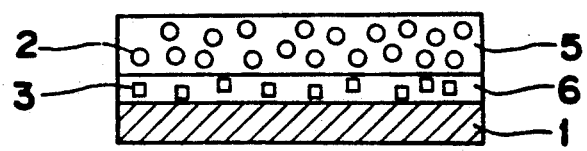
FIG. 2 is a diagram showing the structure of a photosensitive member of function-divided type comprising a charge generating layer and a charge transporting layer which are formed on an electrically conductive substrate.

FIG. 2 shows a photosensitive member of function-divided type comprising a charge generating layer 6 and a charge transporting layer 5. The charge generating layer and the charge transporting layer serve as a photosensitive layer in combination. The charge transporting layer 5 is formed on the surface of the charge generating layer 6. A distyryl compound of the invention is incorporated in the charge transporting layer 5.

Figure 3:
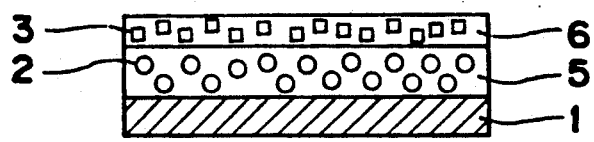
FIG. 3 is a diagram showing the structure of another photosensitive member of the function-divided type comprising a charge generating layer and a charge transporting layer which are formed on an electrically conductive substrate.

FIG. 3 shows another photosensitive member of the function-divided type which, like the one shown in FIG. 2, comprises a charge generating layer 6 and a charge transporting layer 5. In converse relation to the member shown in FIG. 2, the charge generating layer 6 is formed on the surface of the charge transporting layer 5.

Figure 4:
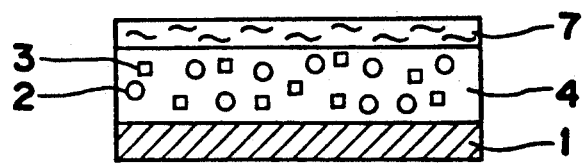
FIG. 4 is a diagram showing the structure of another dispersion-type photosensitive member comprising a photosensitive layer and a surface protective layer formed on an electrically conductive substrate.

The member shown in FIG. 4 comprises the one shown in FIG. 1 and a surface protective layer 7 formed on the surface of the photosensitive layer 4. The photosensitive layer 4 may be separated into a charge generating layer 6 and a charge transporting layer 5 to provide a photosensitive member of the function-divided type.

It is suitable that a surface protective layer is formed with polymer itself such as acrylic resins, polyaryl resins, polycarbonate resins, urethane resins, or formed by dispersing materials with low electrical resistance such as tin oxide or indium oxide. A plasma-polymerized layer of organic compounds may be used as a surface protective layer. The plasma-polymerized layer may contain oxygen atom, nitrogen atom, halogen atom, atom of group III or V in the periodic table. The preferable thickness of the surface protective layer is 5 μm or less.

Figure 5:
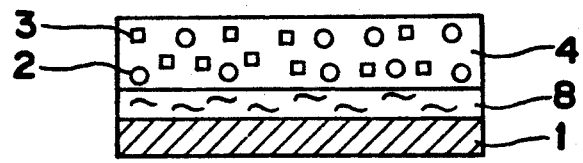
FIG. 5 is a diagram showing the structure of another dispersion-type photosensitive member comprising a photosensitive layer and an intermediate layer formed on an electrically conductive substrate.

FIG. 5 shows a photosensitive member having the same constitution as the one shown in FIG. 1 except that an intermediate layer 8 is interposed between the substrate 1 and the photosensitive layer 4. The intermediate layer 8 serves to give enhanced adhesion, afford improved coatability, protect the substrate and assure injection of charges from the substrate into the photoconductive layer with improved effectiveness.

An intermediate layer is formed with polymer itself such as polyimides, polyamides, nitrocelluloses, polyvinylbutyrals, polyvinylalcohols, or formed by dispersing materials with low electrical resistance such as tin oxide or indium oxide, or by depositing aluminum oxide, zinc oxide, silicon oxide and so on.

The desirable thickness of the intermediate layer is 1 μm or less.

Synthesis of distyryl compound [II-8]

The aldehyde compound represented by the formula below

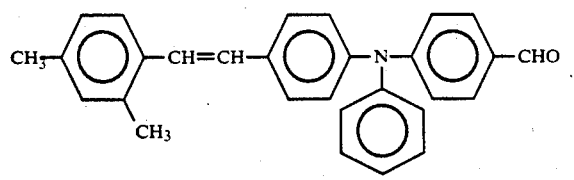

of 4.03 g and the phosphonate represented by the formula below

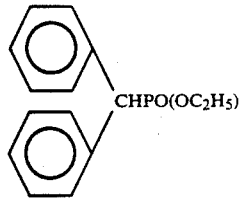

of 3.04 g were dissolved in dimethylformaldehyde of 40 ml. A suspension containing potassium ter-butoxide of 1.68 g in dimethylformamide of 20 ml was added into the above obtained solution while cooling to 5° C. or less. Then, the mixture was stirred for 4 hours at room temperature, and further 2 hours at 80° C. to complete the reaction.

The obtained mixture was poured into ice water of 500 ml to neutralize with hydrochloric acid. After about 30 minutes, the deposited crystals were filtered. The filtered crystals were washed with water and dissolved in benzene. The solution was supplied to silica gel-column chromatograph to separate and purify the aimed compound, distyryl compound [II-8]. Benzene of the effluent was distilled. The residual materials were recrystallized in acetonitrile to obtain pale white-yellow crystals of 2.9 g (yield: 52%) (m.p.: 63–64° C.).

The result of the elemental analysis was as follows.

|  | C (%) | H (%) | N (%) |
|---|---|---|---|
| calc.* | 91.14 | 6.33 | 2.53 |
| found | 91.16 | 6.25 | 2.41 |

*$C_{42}H_{35}N$

Synthesis of distyryl compound [III-2]

The aldehyde compound represented by the formula below

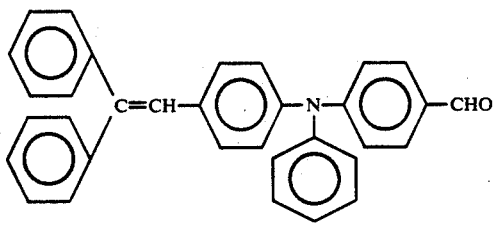

of 4.51 g and ethyl triphenyl phosphonium bromide of 3.71 g were dissolved in dimethylformamide of 100 ml. The solution was added gradually into the dispersion containing potassium ter-butoxide of 2.24 g in dimethylformamide of 50 ml under nitrogen atmosphere while cooling to 5° C. or less.

Then, the mixture was stirred for 4 hours at room temperature, and further 30 minutes at 80° C. to complete the reaction.

The obtained mixture was poured into ice water of 500 ml to neutralize with dilute hydrochloric acid. After about 30 minutes, deposited crystals were filtered. The filtered products were washed with water and dissolved in benzene. The solution was supplied to silica gel-column chromatograph to separate and purify the aimed compound, distyryl compound [III-2]. Benzene of the effluent was distilled. The residual materials were recrystallized in acetonitrile to obtain pale yellow crystals of 3.0 g (yield: 65%) (m.p.: 56–58° C.).

The result of the elemental analysis was as follows.

|  | C (%) | H (%) | N (%) |
|---|---|---|---|
| calc.* | 90.71 | 6.26 | 3.02 |
| found | 90.66 | 6.29 | 2.89 |

*$C_{35}H_{29}N$

Synthesis of distyryl compound [III-11]

The aldehyde compound represented by the formula below

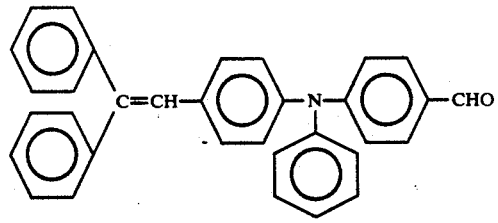

of 4.51 g and the phosphonate represented by the formula below

of 2.18 g were dissolved in dimethylformaldehyde of 60 ml. A suspension containing potassium ter-butoxide of 1.68 g in dimethylformamide of 50 ml was added into the above obtained solution while cooling to 5° C. or less. Then, the mixture was stirred for 2 hours at room temperature, and further one hour at 80° C. to complete the reaction.

The obtained mixture was poured into ice water of 500 ml to neutralize with hydrochloric acid. After about 30 minutes, the deposited crystals were filtered. The filtered products were washed with water and dissolved in benzene/hexane. The solution was supplied to silica gel-column chromatograph to separate and purify the aimed compound, distyryl compound [III-11]. Benzene/hexane of the effluent was distilled. The residual materials were recrystallized in acetonitrile to obtain pale yellow crystals of 3.7 g (yield: 72%) (m.p. 67–68° C.).

The result of the elemental analysis was as follows.

|  | C (%) | H (%) | N (%) |
|---|---|---|---|
| calc.* | 88.54 | 5.63 | 2.72 |

| | C (%) | H (%) | N (%) |
|---|---|---|---|
| found | 88.56 | 5.55 | 2.61 |

*$C_{38}H_{20}NO$

Specific examples are shown below. These examples are shown with no significance in restricting the embodiments of the invention.

"part" means "part by weight" in following Examples so long as it is not particularly specified.

EXAMPLE 1

The bisazo compound represented by the following formula [A]

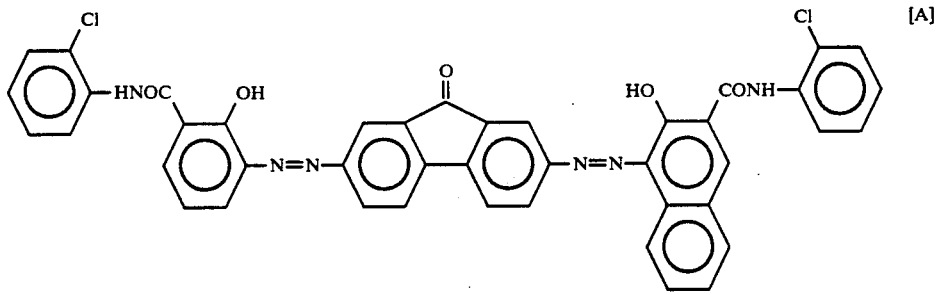

[A]

EXAMPLES 2–4

Photosensitive members with the same structure as that of Example 1 were prepared in a manner similar to Example 1 except that the distyryl compounds [II-3], [II-4] and [II-5] were used respectively instead of the distyryl compound [II-2].

$V_0$, $E_{\frac{1}{2}}$ and $DDR_1$ were measured on the resultant photosensitive members in a manner similar to Example 1.

The results are shown in Table 1.

EXAMPLE 5

The bisazo compound represented by the following formula [B]

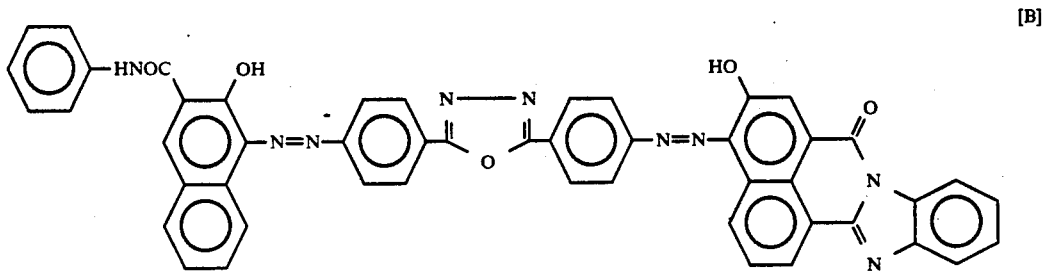

[B]

of 0.45 parts by weight and 0.45 parts by weight of polyester resin (Vylon 200 made by Toyobo K.K.) and 50 parts by weight of cyclohexanone were taken in Sand mill for dispersion. The dispersion solution of the bisazo pigment was applied onto aluminotype-Mylar of 100 μm in thickness by a film applicator to form a charge generating layer so that the thickness of the layer might be 0.3 g/m² after dried. A solution of 50 parts of the distyryl compound [II-2], and 50 parts of polycarbonate resin (K-1300; made by Teijin Kasei K.K.) dissolved in 400 parts of 1,4-dioxane was applied onto the above formed charge generating layer to form a charge transporting layer so that the thickness of the layer might be 16 μm after dried. Thus, a photosensitive member with the two layers was prepared.

The resultant photosensitive member was incorporated into an electrophotographic copying machine (EP-470Z, made by Minolta Camera K.K.) and tested with application of voltage of −6 Kv to d.c. power supply to measure initial surface potential $V_0$ (V), amount of exposure required for $V_0$ to reduce to half of $V_0$ ($E_{\frac{1}{2}}$ (lux.sec)), and potential decay rate $DDR_1$ (%) when the member was allowed to stand in the dark for 1 second after charging.

The results are shown in Table 1.

of 0.45 parts by weight and 0.45 parts by weight of polystyrene (molecular weight; 40000) and 50 parts by weight of cyclohexanone were taken in Sand mill for dispersion. The dispersion solution of the bisazo compound was applied onto aluminotype-Mylar of 100 μm in thickness by a film applicator to form a charge generating layer so that the thickness of the layer might be 0.3 g/m² after dried. A solution of 50 parts of the distyryl compound [II-6], and 50 parts of polyarylate resin (U-100; made by Yunitika K.K.) dissolved in 400 parts of 1,4-dioxane was applied onto the above formed charge generating layer to form a charge transporting layer so that the thickness of the layer might be 20 μm after dried. Thus, a photosensitive member with the two layers was prepared.

$V_0$, $E_{\frac{1}{2}}$, $DDR_1$ were measured on the resultant photosensitive member in a manner similar to Example 1.

The results are shown in Table 1.

EXAMPLES 6–8

Photosensitive members with the same structure as that of Example 5 were prepared in a manner similar to Example 5 except that the distyryl compounds [II-7], [II-8] and [II-9] were used respectively instead of the distyryl compound [II-6].

$V_0$, $E_{\frac{1}{2}}$, $DDR_1$ were measured on the resultant photosensitive members in a manner similar to Example 1.

The results are shown in Table 1.

EXAMPLE 9

The polycyclic quinone compound represented by the following formula [C]

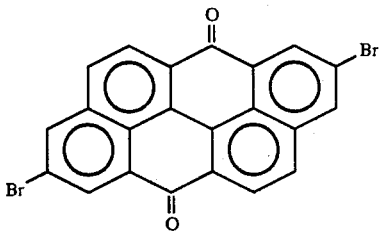

[C]

of 0.45 parts by weight and 0.45 parts by weight of polycarbonate resin (Panlite K-1300: made by Teijin Kasei K.K.) and 50 parts by weight of dichloroethane were taken in Sand mill for dispersion.

The dispersion solution of the polycyclic quinone compound was applied onto aluminotype-Mylar of 100 μm in thickness by a film applicator to form a charge generating layer so that the thickness of the layer might be 0.4 g/m² after dried.

A solution of 60 parts of the distyryl compound [II-10] and 50 parts of polyarylate resin (U-100: made by Yunitika K.K.) dissolved in 400 parts of 1,4-dioxane was applied onto the above formed charge generating layer to form a charge transporting layer so that the thickness of the layer might be 18 μm after dried. Thus, a photosensitive member with the two layers was prepared.

$V_0$, $E_{\frac{1}{2}}$, $DDR_1$ were measured on the resultant photosensitive member in a manner similar to Example 1.

The results are shown in Table 1.

EXAMPLES 10-11

Photosensitive members with the same structure as that of Example 9 were prepared in a manner similar to Example 9 except that the distyryl compounds [II-11] and [II-12] were used respectively instead of the distyryl compound [II-10].

$V_0$, $E_{\frac{1}{2}}$, $DDR_1$ were measured on the resultant photosensitive members in a manner similar to Example 1.

The results are shown in Table 1.

EXAMPLE 12

The perylene pigment represented by the following formula [D]

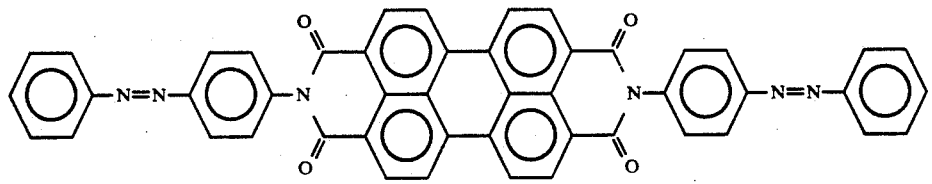

[D]

of 0.45 parts by weight and 0.45 parts by weight of butyral resin (BX-1: made by Sekisui Kagaku Kogyo K.K.) and 50 parts by weight of dichloroethane were taken in Sand mill for dispersion. The dispersion solution of the perylene pigment was applied onto alumino-type-Mylar of 100 μm in thickness by a film applicator to form a charge generating layer so that the thickness of the layer might be 0.4 g/m² after dried. A solution of 50 parts of the distyryl compound [II-13] and 50 parts of polycarbonate resin (PC-Z made by Mitsubishi Gas Kagaku K.K.) dissolved in 400 parts of 1,4-dioxane was applied onto the above formed charge generating layer to form a charge transporting layer so that the thickness of the layer might be 18 μm after dried. Thus, a photosensitive member with the two layers was prepared.

$V_0$, $E_{\frac{1}{2}}$ and $DDR_1$ were measured on the resultant photosensitive members in a manner similar to Example 1.

The results are shown in Table 1.

EXAMPLES 13-14

Photosensitive members with the same structure as that of Example 12 were prepared in a manner similar to Example 12 except that the distyryl compounds [II-17] and [II-20] were used respectively instead of the distyryl compound [II-13].

$V_0$, $E_{\frac{1}{2}}$, $DDR_1$ were measured on the resultant photosensitive members in a manner similar to Example 1.

The results are shown in Table 1.

EXAMPLE 15

Titanylphthalocyanine of 0.45 parts by weight and 0.45 parts by weight of butyral resin (BX-1; made by Sekisui Kagaku Kogyo K.K.) and 50 parts by weight of dichloroethane were taken in Sand mill for dispersion. The dispersion solution of the phthalocyanine pigment was applied onto aluminotype-Mylar of 100 μm in thickness by a film applicator to form a charge generating layer so that the thickness of the layer might be 0.3 g/m² after dried. A solution of 50 parts of the distyryl compound [II-21] and 50 parts of polycarbonate resin (PC-Z: made by Mitsubishi Gas Kagaku K.K.) dissolved in 400 parts of 1,4-dioxane was applied onto the above formed charge generating layer to form a charge transporting layer so that the thickness of the layer might be 18 μm after dried. Thus, a photosensitive member with the two layers was prepared.

$V_0$, $V_{\frac{1}{2}}$ and $DDR_1$ were measured on the resultant photosensitive members in a manner similar to Example 1.

The results were shown in Table 1.

EXAMPLE 16-17

Photosensitive members with the same structure as that of Example 15 were prepared in a manner similar to Example 15 except that the distyryl compounds [II-23] and [II-25] were used respectively instead of the distyryl compound [II-21].

$V_0$, $E_{\frac{1}{2}}$, $DDR_1$ were measured on the resultant photosensitive members in a manner similar to Example 1.

The results are shown in Table 1.

EXAMPLE 18

Copper-phthalocyanine of 50 parts and tetranitro-copper-phthalocyanine of 0.2 parts were dissolved in conc.sulfuric acid (98%) of 500 parts while stirring. The obtained solution was poured into water of 5000 parts to deposit a photoconductive composition of copper-phthalocyanine and tetranitro-copper-phthalocyanine. The deposited composition was filtered, washed with water and dried in vacuum at 120° C.

The obtained composition of 10 parts, a thermosetting acrylic resin (Acrydick A405; made by Dainippon Ink K.K.) of 22.5 parts, a melamine resin (Super Beckamine J820; made by Dainippon Ink K.K.) of 7.5 parts, a distyryl compound [II-28] of 15 parts, a mixed solvent (methyl ethyl ketone : xylene=1:1) of 100 parts were taken into a ball mill for dispersion for 48 hours to obtain a photosensitive coating solution. The coating solution was applied onto an aluminum substrate to form a photosensitive layer of about 15 μm in thickness after dried.

The resultant photosensitive member was tested with the application of voltage of +6KV to d.c. power to measure $V_0$, $E_{\frac{1}{2}}$, $DDR_1$.

The results are shown in Table 1.

EXAMPLES 19–21

Photosensitive members with the same structure as that of Example 18 were prepared in a manner similar to Example 18 except that the distyryl compounds [II-29], [II-32] and [II-33] were used respectively instead of the distyryl compound [II-28].

$V_0$, $E_{\frac{1}{2}}$ and $DDR_1$ were measured on the resultant photosensitive members in a manner similar to the Example 18.

The results are shown in Table 1.

EXAMPLES 22–25

Photosensitive members with the same structure as that of Example 1 were prepared in a manner similar to Example 1 except that the distyryl compounds [III-2], [III-3], [III-4] and [III-8] were used respectively instead of the distyryl compound [II-2].

$V_0$, $E_{\frac{1}{2}}$, $DDR_1$ were measured on the resultant photosensitive members in a manner similar to the Example 1.

The results are shown in Table 1.

EXAMPLES 26–29

Photosensitive members with the same structure as that of Example 5 were prepared in a manner similar to Example 5 except that the distyryl compounds [III-10], [III-11], [III-14] and [III-16] were used respectively instead of the distyryl compound [II-6].

$V_0$, $E_{\frac{1}{2}}$ and $DDR_1$ were measured on the resultant photosensitive members in a manner similar to Example 1.

The results are shown in Table 1.

EXAMPLES 30–32

Photosensitive members with the same structure as that of Example 9 were prepared in a manner similar to Example 9 except that the distyryl compounds [III-17], [III-18] and [III-20] were used respectively instead of the distyryl compound [II-10].

$V_0$, $E_{\frac{1}{2}}$ and $DDR_1$ were measured on the resultant photosensitive members in a manner similar to Example 1.

The results are shown in Table 1.

EXAMPLES 33–35

Photosensitive members with the same structure as that of Example 12 were prepared in a manner similar to Example 12 except that the distyryl compounds [III-28], [III-31] and [III-32] were used respectively instead of the distyryl compound [II-13].

$V_0$, $E_{\frac{1}{2}}$ and $DDR_1$ were measured on the resultant photosensitive members in a manner similar to Example 1.

The results are shown in Table 1.

EXAMPLES 36–38

Photosensitive members with the same structure as that of Example 15 were prepared in a manner similar to Example 15 except that the distyryl compounds [III-35], ]III-37] and [III-39] were used respectively instead of the distyryl compound [II-21].

$V_0$, $E_{\frac{1}{2}}$ and $DDR_1$ were measured on the resultant photosensitive members in a manner similar to Example 1.

The results are shown in Table 1.

EXAMPLES 39–42

Photosehsitive members with the same structure as that of Example 18 were prepared in a manner similar to Example 18 except that the distyryl compounds [III-41], [III-44], [III-45] and [III-47] were used respectively instead of the distyryl compound [II-28].

$V_0$, $E_{\frac{1}{2}}$ and $DDR_1$ were measured on the resultant photosensitive members in a manner similar to Example 1.

The results are shown in Table 1.

COMPARATIVE EXAMPLES 1–7

Photosensitive members with the same structure as that of Example 18 were prepared in a manner similar to Example 18 except that the compounds (F), (G), (H), (I), (J), (K), (L) were used respectively instead of the distyryl compound [II-28].

$V_0$, $E_{\frac{1}{2}}$ and $DDR_1$ were measured on the resultant photosensitive members in a manner similar to Example 18.

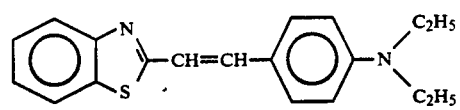

[F]

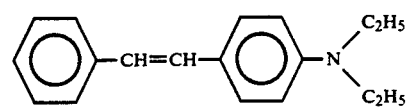

[G]

-continued
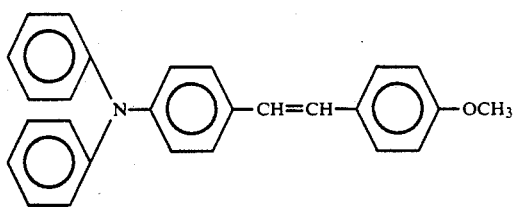
[H]
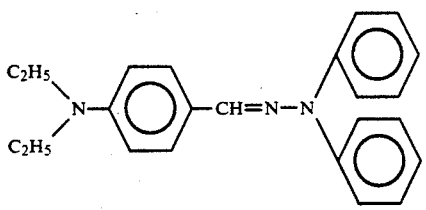
[I]
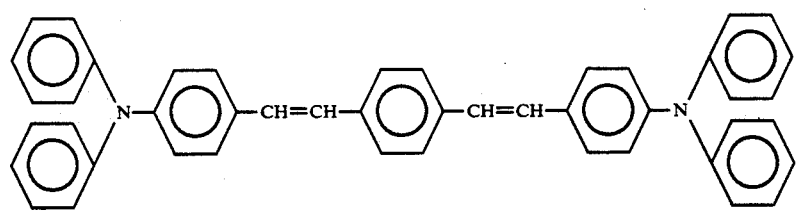
[J]
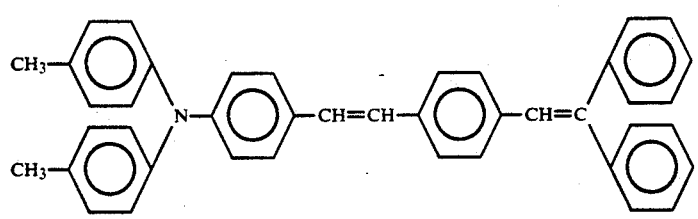
[K]
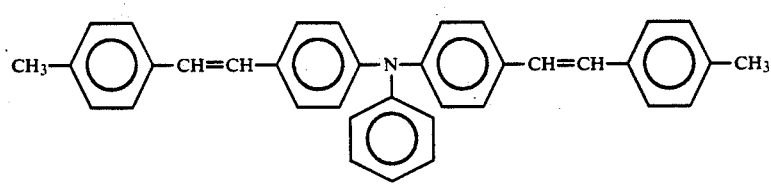
[L]
| TABLE 1 | | | |
|---|---|---|---|
| Example No. | $V_o$ (v) | $E_{\frac{1}{2}}$ (lux · sec) | $DDR_1$ (%) |
| 1 | −650 | 1.0 | 3.0 |
| 2 | −650 | 1.3 | 3.2 |
| 3 | −640 | 1.1 | 3.5 |
| 4 | −650 | 0.8 | 3.0 |
| 5 | −660 | 0.9 | 3.1 |
| 6 | −640 | 0.8 | 3.4 |
| 7 | −650 | 1.0 | 3.0 |
| 8 | −660 | 1.2 | 3.0 |
| 9 | −640 | 1.1 | 3.5 |
| 10 | −650 | 1.0 | 3.2 |
| 11 | −660 | 0.8 | 2.9 |
| 12 | −650 | 0.9 | 3.0 |
| 13 | −650 | 0.9 | 3.1 |
| 14 | −660 | 0.8 | 2.8 |
| 15 | −650 | 1.2 | 2.9 |
| 16 | −640 | 0.9 | 3.4 |
| 17 | −650 | 1.0 | 3.0 |
| 18 | +610 | 1.0 | 13.0 |
| 19 | +610 | 0.9 | 12.2 |
| 20 | +600 | 0.8 | 13.2 |
| 21 | +610 | 1.0 | 12.7 |
| 22 | −650 | 1.2 | 3.0 |
| 23 | −640 | 1.0 | 3.4 |
| 24 | −650 | 1.2 | 2.9 |
| 25 | −660 | 1.1 | 2.8 |
| 26 | −650 | 1.0 | 3.1 |
| 27 | −650 | 1.0 | 3.0 |
| 28 | −660 | 1.3 | 2.9 |
| 29 | −650 | 0.9 | 3.2 |
| 30 | −640 | 0.8 | 3.5 |
| 31 | −660 | 1.0 | 3.0 |
| 32 | −650 | 0.7 | 3.0 |
| 33 | −640 | 1.3 | 3.5 |
| 34 | −660 | 1.2 | 3.1 |
| 35 | −650 | 1.1 | 3.0 |
| 36 | −650 | 1.3 | 3.0 |
| 37 | −640 | 1.0 | 3.5 |
| 38 | −650 | 1.2 | 3.2 |
| 39 | +610 | 1.3 | 12.5 |
| 40 | +600 | 1.0 | 13.0 |
| 41 | +610 | 0.9 | 12.7 |
| 42 | +610 | 1.1 | 12.2 |
| Comparative Example No. | | | |
| 1 | +620 | 15.0 | 12.0 |
| 2 | +610 | 10.2 | 11.5 |

TABLE 1-continued

| | $V_o$ (v) | $E_{\frac{1}{2}}$ (lux·sec) | $DDR_1$ (%) |
|---|---|---|---|
| 3 | +600 | 6.5 | 13.7 |
| 4 | +600 | 3.2 | 14.3 |
| 5 | +620 | 13.4 | 9.8 |
| 6 | +600 | 3.5 | 13.0 |
| 7 | +610 | 3.0 | 12.4 |

Even though a photosensitive member of the present invention is a monolayer type or a laminated type, it has a sufficient charge keeping ability. The potential decay rate in the dark is so small that a photosensitive member of the invention can be put into practical use. The photosensitive member of the invention is excellent in sensitivity.

The photosensitive members prepared in the examples 18 and 39 were respectively installed in a copying machine (EP-350Z made by Minolta Camera K.K.) to be subjected to a copying repetition test when charged positively. Even after the copying process was repeated 1000 times in each of the examples 18 and 39, copied images were as clear and excellent in gradient as those of initial copied images. The sensitivity did not change during the repetition test. It is understood that a photosensitive member of the present invention is stable in repetition properties.

What is claimed is:

1. A photosensitive member comprising an electrically conductive substrate; and
   a photosensitive layer formed on or over the substrate and comprising a charge generating material and a distyryl compound represented by the general formula [I]

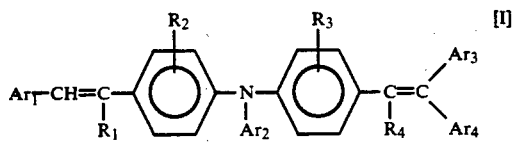

in which
   $Ar_1$ is a hydrogen atom, an alkyl group, an aralkyl group, an alkenyl group, an alkynyl group, or a heterocyclic group, wherein the aryl group and the heterocyclic group may have a substituent;
   $Ar_2$ is an alkyl group, an aralkyl group or an aryl group, each of which may have a substituent;
   $Ar_3$ and $Ar_4$ are independently an alkyl group, an aryl group, an aralkyl group or a heterocyclic group, each of which may have a substituent;
   $R_1$ and $R_4$ are a hydrogen atom, an alkyl group, an aryl group, an aralkyl group;
   $R_2$ and $R_3$ are a hydrogen atom, an alkyl group, an alkoxy group or a halogen atom.

2. A photosensitive member of claim 1, wherein the photosensitive layer comprises a charge transporting layer comprising said distyryl compound and a charge generating layer comprising said charge generating material.

3. A photosensitive member of claim 2, wherein the charge generating layer is 4 μm or less in thickness.

4. A photosensitive member of claim 2, wherein the charge transporting layer is 3–30 μm in thickness.

5. A photosensitive member of claim 2, the charge transporting layer comprises the distyryl compound dispersed in a resin.

6. A photosensitive member of claim 5, wherein the charge transporting layer contains the distyryl compound at the content of 0.2–2 parts by weight on the basis of 1 part by weight of the resin.

7. A photosensitive member of claim 5, wherein the volume resistance of the resin is $1 \times 10^{12}$ Ω·cm or more.

8. A photosensitive member of claim 1, wherein the photosensitive layer comprises the distyryl compound and the charge generating material which are dispersed in a resin.

9. A photosensitive member of claim 8, wherein the photosensitive layer is 3–30 μm in thickness.

10. A photosensitive member of claim 8, wherein the photosensitive layer contains the charge generating material at the content of 0.01–2 parts by weight on the basis of 1 part by weight of the resin.

11. A photosensitive member of claim 8, wherein the volume resistance of the resin is $1 \times 10^{12}$ Ω·cm or more.

12. A photosensitive member of claim 1, wherein a surface protective layer is formed on the photosensitive layer.

13. A photosensitive member of claim 1, wherein an intermediate layer is formed between the electrically conductive substrate and the photosensitive layer.

14. A photosensitive member comprising an electrical conductive substrate; and
    a photosensitive layer formed on or over the substrate and comprising a charge generating material and a distyryl compound represented by the general formula [II]

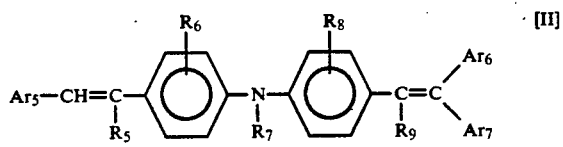

in which
   $Ar_5$ and $Ar_6$ are an aryl group or a heterocyclic ring group, each of which may have a substituent;
   $R_7$ and $Ar_7$ are an alkyl group, an aralkyl group or an aryl group, each of which may have a substituent;
   $R_6$ and $R_8$ are independently a hydrogen atom, an alkyl group, an alkoxy group or a halogen atom;
   $R_5$ and $R_9$ are a hydrogen atom, an alkyl group, an aralkyl group or an aryl group.

15. A photosensitive member of claim 14, wherein $Ar_5$ and $Ar_6$ are independently a phenyl group or a heteromonocyclic group.

16. A photosensitive member of claim 14, wherein $R_5$ and $R_9$ are independently a hydrogen atom.

17. A photosensitive member of claim 14, wherein $Ar_6$ and $Ar_7$ are independently a phenyl group or an alkyl group.

18. A photosensitive member comprising an electrically conductive substitute; and
    a photosensitive layer formed on or over the substrate and comprising a charge generating material and a distyryl compound represented by the general formula [III]

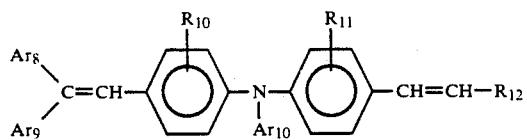

[III]

in which

Ar$_8$ and Ar$_9$ are independently an alkyl group or an aryl group, each of which may have a substituent;

Ar$_{10}$ is an alkyl group, an aralkyl group, or an aryl group, each of which may have a substituent;

R$_{10}$ and R$_{11}$ are independently a hydrogen atom, an alkyl group, an alkoxy group or a halogen atom;

R$_{12}$ is a hydrogen atom, an alkyl group, a residual group selected from the group consisting of thiophene, furan pyrrole and pyridine, an aralkyl group, an alkenyl group or an alkynyl group.

* * * * *